(12) United States Patent
Yoo

(10) Patent No.: US 8,993,487 B2
(45) Date of Patent: *Mar. 31, 2015

(54) BIO DISC, BIO-DRIVER APPARATUS, AND ASSAY METHOD USING THE SAME

(75) Inventor: Jae Chern Yoo, Pohang-si (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 1669 days.

This patent is subject to a terminal disclaimer.

(21) Appl. No.: 11/919,567

(22) PCT Filed: May 2, 2006

(86) PCT No.: PCT/KR2006/001658
§ 371 (c)(1),
(2), (4) Date: May 27, 2010

(87) PCT Pub. No.: WO2006/118420
PCT Pub. Date: Nov. 9, 2006

(65) Prior Publication Data
US 2010/0234237 A1 Sep. 16, 2010

(30) Foreign Application Priority Data

Apr. 30, 2005 (KR) .................. 10-2005-0036983

(51) Int. Cl.
*C40B 60/12* (2006.01)
*C12Q 1/68* (2006.01)
*B01L 3/00* (2006.01)
*F16K 99/00* (2006.01)

(52) U.S. Cl.
CPC .............. *C12Q 1/686* (2013.01); *B01L 3/50273* (2013.01); *B01L 3/502738* (2013.01); *F16K 99/0001* (2013.01); *B01L 2200/10* (2013.01); *B01L 2200/143* (2013.01); *B01L 2300/0806* (2013.01); *B01L 2400/0409* (2013.01); *B01L 2400/043* (2013.01); *B01L 2400/0633* (2013.01)
USPC .......................................................... 506/39

(58) Field of Classification Search
None
See application file for complete search history.

(56) References Cited

U.S. PATENT DOCUMENTS

| 5,863,708 A | 1/1999 | Zanzucchi et al. | |
|---|---|---|---|
| 2003/0012693 A1 | 1/2003 | Otillar et al. | |
| 2003/0059803 A1* | 3/2003 | Werner et al. | 435/6 |
| 2003/0138941 A1* | 7/2003 | Gong et al. | 435/287.2 |
| 2004/0155213 A1* | 8/2004 | Yoo | 251/65 |

FOREIGN PATENT DOCUMENTS

| EP | 0 086 442 A1 | 8/1983 | |
|---|---|---|---|
| EP | 1 508 368 A1 | 2/2005 | |
| JP | 61-31780 | * | 2/1986 |
| JP | 61-31780 | * | 2/1996 |
| JP | 8-121636 | | 5/1996 |
| JP | 2003-84001 | | 3/2003 |
| JP | 2004-73995 | | 3/2004 |
| WO | 02-097422 | | 12/2002 |
| WO | 03/080868 | | 10/2003 |
| WO | 03/080868 A1 | | 10/2003 |
| WO | WO 03/080868 | | 10/2003 |

OTHER PUBLICATIONS

Shimizu, JP 08138932 A, Translated abstract for JP 61-31780, obtained from EAST Dec. 10, 2011, pp. 1-2.*
Shimizu JP 361031780A, Translated abstract for JP 61-31780, obtained from EAST Dec. 10, 2011, pp. 1-2.*
McDonald et al., "A Magnetically Driven PDMS Micropump with Micro-Ball Valve"; Sep. 1-5, 2004, Proceedings of the 26th Annual International Conference of the IEEE EMBS, pp. 2650-2653).*
Chinese Office Action issued Jan. 29, 2010 in corresponding Chinese Patent Application 200680014437.4.
Ralf Lenigk et al., "Surface Characterization of a Silicon-Chip-Based DNA Microarray", Langmuir 2001, 17, American Chemical Society, pp. 2497-2501.
Hidenori Nagai et al., "High-throughput PCR in silicon based microchamber array", Biosensors & Bioelectronics 16, Elsevier Science B.V., 2001, pp. 1015-1019.
Japanese Office Action issued Jan. 28, 2011 in corresponding Japanese Patent Application 2008-508759.
Japanese Office Action received Jul. 6, 2010 in corresponding Japanese Patent Application No. 2008-508759.
Kwang W Oh, et al, "Topical Review; A review of Microvalves", Journal of Micromechanics & Microengineering, Institute of Physics Publishing, Bristol, GB, vol. 16, No. 5, May 1, 2006, pp. R13-R39.
European Search Report mailed Aug. 21, 2009 and issued in corresponding European Patent Application 06757618.1.

* cited by examiner

*Primary Examiner* — Karlheinz R Skowronek
*Assistant Examiner* — Lianko Garyu
(74) *Attorney, Agent, or Firm* — Staas & Halsey LLP

(57) ABSTRACT

A bio-disc device including new valve control means and fluid movement system, a bio-driver apparatus in which a controller disc including a controller for the bio-disc is installed, and an assay method using the same, which are suitable for labs-on-a-chips for various diagnostic assays, nucleic acid hybridization assays, and immunoassays, are provided. The bio-driver apparatus is compatible with general optical discs, including audio CDs, CD-Rs, game CDs, DVDs, etc., and the assay method is compatible with general optical disc drivers, including CD-ROMs, DVD players, etc. Thus, the bio-driver apparatus and the assay method offer and economical and convenient alternative to existing products. In addition, the bio-driver apparatus can be readily and easily applied in connection with a computer for remote diagnosis via the Internet.

47 Claims, 19 Drawing Sheets

Fig. 1
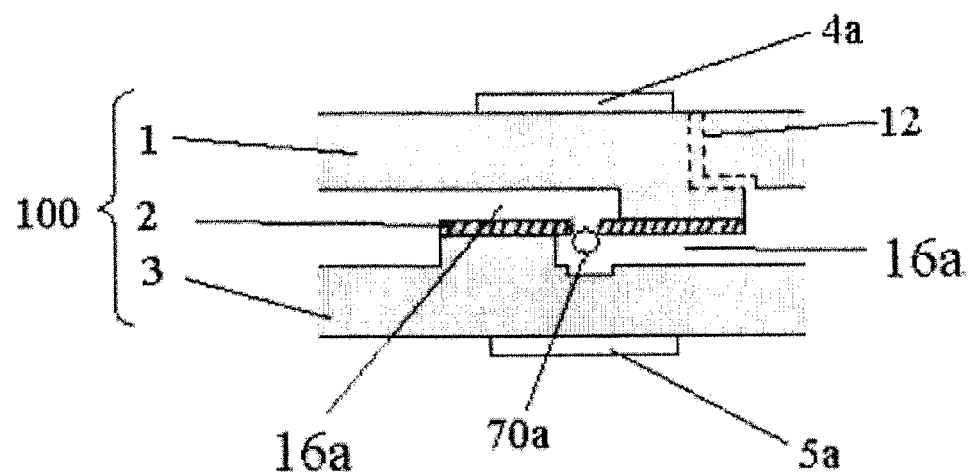
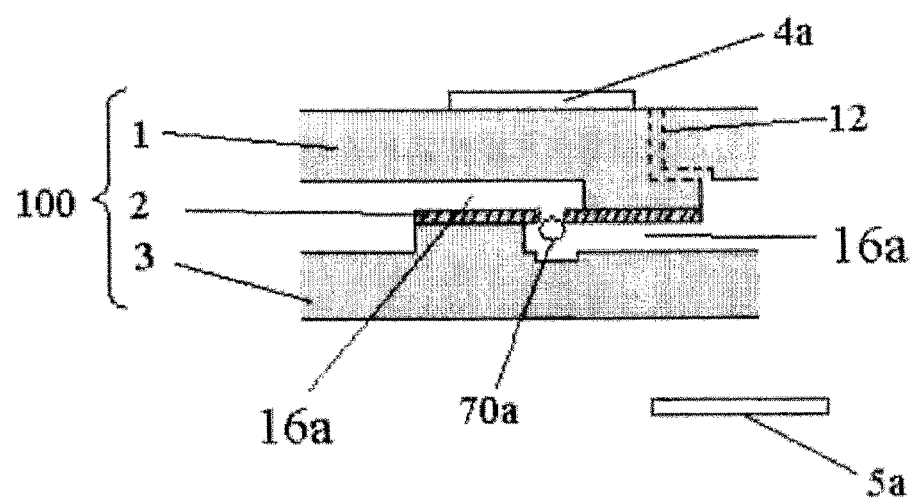
Fig. 2
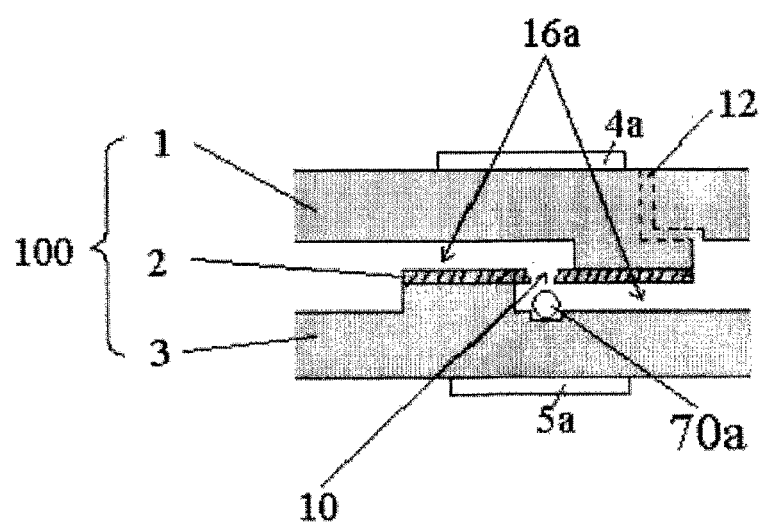

BIO DISC, BIO-DRIVER APPARATUS, AND ASSAY METHOD USING THE SAME

CROSS-REFERENCE TO RELATED APPLICATIONS

This application claims the benefit of PCT Application No. PCT/KR2006/001658, filed May 2, 2006 and Korean Application No. 10-2005-0036983, filed Apr. 30, 2005 in the Korean Intellectual Property Office, the disclosures of which are incorporated herein by reference.

BACKGROUND

1. Field

The present invention relates to a bio-disc comprising new valve control means and fluid movement system, a bio-disc device including the bio-disc, a bio-driver apparatus, and an assay method using the same. More particularly, the present invention relates to a bio-disc with a lab-on-a-chip for various diagnostic assays, nucleic acid hybridization assays, or immunoassays, a bio-driver apparatus integrated with a controller disc including a controller for the bio-disc, and an assay method using the same.

2. Description of the Related Art

The present invention relates to a continued application of International Patent Application No. PCT/KR02/00126, which was filed 27 Jan. 2002 and claims the priority of Korean Patent Application No. 10-2001-0003956, filed 27 Jan. 2001, and International Patent Application No. PCT/KR02/01035, which was filed 31 May 2002 and claims the priority of Korean Patent Application No. 10-2001-0031284, filed 31 May 2001. International Patent Application No. PCT/KR02/00126 and its priority Korean application are entitled "Nucleic acid hybridization assay method and device using cleavage technique responsive to complementary double strand or single strand of nucleic acids or oligonucleotides", and International Patent Application No. PCT/KR02/01035 and its priority Korean application are entitled "Micro valve apparatus using microbead and method for controlling the same". The disclosures of the above previous applications are incorporated herein by reference in their entirety.

The nucleic acid hybridization assay method and device using a cleavage technique responsive to a complementary double strand or single strand of-nucleic acids are applicable to diverse quantitative or qualitative assay devices. In addition, the micro valve is an essential element to control the flow of fluid in a lab-on-a-chip.

The nucleic acid assay device may comprise a detector including an optical device, an electrochemical device, or a capacitance and impedance measurement device to detect or cleaved signal elements. The detected results can be digitized as computer executable software and provided through an established communications network, such as the Internet, to a patient or a doctor. In this manner, a remote diagnostic system ensuring convenience to both patient and doctor can be implemented based on the nucleic acid assay device. A capacitance and impedance measurement for the detector may include interdigitated array electrodes with cleavable signal elements, as disclosed in the previous application.

The present invention relates to a non-optical bio-disc, a bio-disc device, a bio-driver apparatus, and an assay method using the same, which are applicable to various kinds of diagnostic assay devices, nucleic acid hybridization assay devices, and immunoassay devices.

Most clinical diagnostic assay devices developed so far for the detection of small quantities of analytes in fluids are used in serial or parallel connection with multiple-sample preparation and automated reagent addition devices for the simultaneous analysis of numerous test samples with higher efficiency. Such automated reagent preparation devices and automated multiplex analyzers are often integrated into a single device.

Clinical laboratory analyzers of this type can accurately perform hundreds of assays using small quantities of samples and reagents in one hour automatically or semi-automatically. However, these analyzers are expensive and only centralized laboratories and hospitals can afford them. Such centralization necessitates sample transport to the laboratory or hospital and often precludes urgent or emergent analysis of time-critical samples.

Thus, to address these problems, there is an increasing need for clinical analyzers which are cheap and easy-to-handle for everyone, such as clinical analyzers suitable for use at the patient bedside of in the patient's home without dedicated detectors.

<Optical and Non-Optical Bio-Discs>

The standard compact disk is formed from a 12-cm polycarbonate substrate, a reflective metal layer, and a protective lacquer coating. DVD stands for digital video disk, a type of optical disk of the same size as the compact disk, but with significantly greater recording capacity.

The polycarbonate substrate is optical-quality clear polycarbonate. In a standard pressed CD or DVD, the data layer is part of the polycarbonate substrate, and the data are impressed as a series of pits by a stamper during injection molding. In the injection molding process, melted polycarbonate is injected into a mold under high pressure and cooled in a mirror image of the mold or stamper. As a result, reverse pits of the stamper are formed on the polycarbonate disk surface during mastering as binary data. The stamping master is typically glass.

As is widely known to one of ordinary skilled in the art, information written to general optical discs, such as audio CDs, game CDs, refractivity in their dye layer. In a common CD using a differential reflectivity detection method, indentations of pits are formed in the CD to a depth on the order of one-eighth to one-quarter of the wavelength of an incident laser beam. The indentations cause destructive interference in a reflected beam and correspond to bits having a "0" value. Flat areas of the CD reflect the incident laser beam toward a detector and correspond to bits having a "1" value.

U.S. Pat. No. 5,580,696 discloses materials of a dye layer for optical discs using refractivity-based data detection. An optical disk using the dye layer is rotated about a rotary shaft and scanned by laser to read data from the dye layer.

However, a general optical pickup for the above-described optical discs includes both a light emitting unit and a light receiving unit in a single module. In this structure, its optical traveling path is relatively long, and there is a poor sensitivity problem of the light receiving unit. In addition, laser scanning for information reading requires actuating the optical pickup to a predetermined location on an optical disc and rotating the optical disc. Furthermore, when such an optical disc read by laser scanning is applied to a bio-assay device, problems such as physical deformation of probes and inaccurate assay results occur.

Various technologies regarding CD-based assay devices have been disclosed: "Optical confocal compact scanning optical microscope based on compact disc technology" (Applied Optics, Vol. 30, No. 10, 1991), "Gradient-index objectives for CD applications" (Applied Optics, Vol. 26, Issue 7, 1987), and "Miniature scanning optical microscope based on compact disc technology" (Proc. Soc. Photo-opt. instrument Eng. page 1139-1169, 1989).

Patents regarding CD-based assay devices include U.S. Pat. No. 4,279,862 entitled "Centrifugal photometric analyzer" (published on 21 Jul. 1981) and U.S. Pat. No. 4,141, 954 entitled "Reaction tube assembly for automatic analyzer" (published on 27 Feb. 1979).

GB 1075800 (published on 12 Jul. 1967), entitled "Disc for centrifuge", discloses a device for flowing a sample fluid supplied via n inject hole of a disc over its surface by centrifugal force. EP 3335946 (published on 12 Apr. 1965), entitled "Separating disks for centrifuge", discloses an apparatus for separating fluid samples injected via an inject hole of a disc by inducing flow of the samples through channels or chambers formed in the disc by centrifugal force.

U.S. Pat. No. 4,311,039 (published on 19 Jan. 1982), entitled "Disc centrifuge photosedimentometer", discloses a disc type chemical assay device using centrifugal force and optical detection.

However, the above-listed conventional assay devices failed to ensure perfect automation in assay and diagnosis and are unsuitable for a lab-on-a-chip.

Unlike the conventional optical discs using differential reflection from physical pits or the refractivity in dye layers, a bio-disc according to the present invention reads information using light transmission, capacitance and impedance measurements, or electrochemical detection, wherein the bio-disc includes chambers as fluid reservoirs and channels as flow paths. Such a bio-disc according to the present invention is referred to as a "non-optical bio-disc", in contrast to the conventional "optical" bio-discs using the differential reflection of laser light scanned over the bio-disc. The conventional ones could not detect information using light transmission due to their structure which includes a reflective metal layer and a dye layer.

The term "non-optical bio-disc" throughout the specification refers to a bio-disc which allows for selective detection of analytic sites using light transmission, capacitance and impedance measurements, or electrochemical detection, without need to rotate the bio-disc and scan it with laser light. Therefore, the "non-optical bio-disc" of the present invention could involve optical assay detectors.

The term "optical bio-disc" throughout the specification refers to a bio-disc using a common optical pickup scanning laser light over the bio-disc to read data from its differential reflectance.

Common polycarbonate substrates can be modified to suit to bio-discs, which are thin film type assay devices, for detecting a small quantity of an analyte in a fluid sample for the diagnostic purpose. In this case, instead of pits and a dye layer, channels as fluid flow paths and chambers as buffer reservoirs are formed in a surface of a polycarbonate substrate through injection molding. In addition, micro valves for controlling fluid flow through the channel and flow rate and an electronic controlling method of the micro valves are needed.

In a bio-disc according to the present invention, channels as fluid flow paths and chambers as buffer reservoirs may be formed in a silicon wafer using semiconductor manufacturing processes. Such a bio-disc according to the present invention includes an electronic circuit integrated into the silicon wafer to control fluid flow and flow rate.

SUMMARY

Additional aspects and/or advantages will be set forth in part in the description which follows and, in part, will be apparent from the description, or may be learned by practice of the invention.

According to an aspect of the present invention, there is provided a bio-disc comprising: a sample inlet; a chamber which reserves a buffer solution or a reaction solution; an assay site where bio materials are arrayed on a substrate; channels through which fluid flows between the sample inlet, the chamber, and the assay site; a hole which connects the channels; and a valve which is used to open and close the hole, wherein the valve is constructed with a micro bead, a permanent magnet disposed above the micro-bead, and an electromagnetic or movable permanent magnet disposed under the micro bead.

The term "assay site" used throughout the specification is referred to as an "array chamber" having a meaning that bio materials are arrayed thereon, or a "hybridization chamber" or an "antigen-antibody reaction chamber" having a meaning that a specific binding reaction of two bio materials, a ligand-receptor reaction, a hybridization reaction, or an antigen-antibody reaction takes place therein.

In the bio-disc according to the present invention, when the micro-bead is located under the hole, the valve is closed by an attractive force between the micro-bead and a film-like permanent magnet disposed above the micro-bead, and the hole of the valve is opened by an attractive force between the micro-bead and the electromagnetic or the moveable permanent magnet disposed under the micro-bead. When the micro-bead is located above the hole, the hole are opened and closed in a reverse arrangement. Since the film-like permanent magnet disposed above the micro-bead is not movable, the hole is always closed by the attractive force between the micro-bead and the film-like permanent magnet. Therefore, the hole of the bio-disc under distribution is always closed, so that it is possible to prevent liquid in the chamber from leaking.

In the bio-disk according to the present invention, a permanent magnet may be provided to only one of upper and lower portions of the valve. Alternatively, permanent magnets may be provided to both of the upper and lower portions of the valve. In a case where the permanent magnets are provided to both of the upper and lower portions of the valve, the movable permanent magnet may be used as a substitute of an optical pickup module of a general addressable optical pick up apparatus. Alternatively, the movable permanent magnet together with the optical module may be mounted. A conventional valve mechanism is controlled by using two electromagnetic magnets disposed above and under a micro-bead, so that there is a problem of complexity in control of the electromagnetic magnets and a large amount of heat generated at the time of applying electricity. In the valve mechanism according to the present invention, one permanent magnet and one electro-magnet are used, or two permanent magnets are used. Therefore, it is possible to reduce generated heat and production cost and to obtain a strong magnetic field. In particular, since the movable permanent magnet is provided to a general addressable optical pickup apparatus, it is possible to move the moveable permanent magnet to a predetermined position of the valve.

In the bio-disc according to the present invention, any material which can be moved by a magnetic field and any shape which can open and close the hole may be used as the micro-bead. Preferably, the micro-bead may be a film-like cylindrical magnet or a film-like cylindrical magnet coated with a cushion material. The cushion material may be a polymer having elasticity such as a rubber. Due to the cushion material, it is possible to more securely close the hole.

According to another aspect of the present invention, there is provided a bio-disc comprising: a sample inlet; a chamber which reserves a buffer solution or a reaction solution; an assay site where bio materials are arrayed on a substrate;

channels through which fluid flows between the sample inlet, the chamber, and the assay site; a hole which connects the channels; and a valve which is used to open and close the hole, wherein the substrate in the assay site is a porous membrane, and wherein a before channel of a just-before valve of the assay site is a hydrophobic channel, and an after channel is a hydrophilic channel.

In the bio-disc according to the present invention, the porous membrane may be any membrane having a large number of pores. Preferably, the porous membrane may be one selected from a group consisting a NC (nitrocellose) membrane, a nylon membrane, and aligned nanotubes. Due to the porous membrane according to the present invention, a surface area of the assay site can be increased, so that a large amount of bio material can be combined. Accordingly, it is possible to increase a sensitivity.

In the bio-disc according to the present invention, the hydrophilic channel may be any channel where a hydrophilic material exists on a surface thereof. Preferably, the hydrophilic channel may be constructed by coating a surface of a hydrophobic channel with a hydrophilic acrylate, an ultra-hydrophilic poly (N-isopropylacrylamide) (PIPAAm) or an optical catalyst selected from a group consisting $ZrO_2$, ZnO, $Fe_2O_3$, and $TiO_2$ or by performing a surface modification on the hydrophobic channel with plasma. The optical catalyst may employ $ZrO_2$, ZnO, $Fe_2O_3$, $TiO_2$, or others. The $TiO_2$ is an affluent mineral in the earth. The $TiO_2$ is inexpensive, stable, and harmless to a human body. When a surface of the $TiO_2$ optical catalyst is illuminated with UV light, a contact angle with respect to water molecule is lowered down to 5 degrees, the water spread entirely over the surface, so that an ultra-hydrophilic phenomenon appears. Here, the term "hydrophilic" means that the contact angle between the surface of the substrate and water droplet spread on the surface thereof becomes less than 20 degrees. The term "ultra-hydrophilic" means that the contact angle becomes less than 10 degrees.

In the bio-disc according to the present invention, the hydrophilic channel is divided into at least one branch channel, and the hydrophilic channel is connected to the porous membrane through a hole provided to a distal end of the branch channel. In a case where there are a plurality of the branch channels, the branch channels may be located at the centers of the spots where the probes are fixed in the assay site.

In the bio-disc according to the present invention, the assay site may have air holes disposed at the both sides of the assay site to dry the porous membrane. When the disc is rotated, air can be automatically absorbed or vented to or from the air holes disposed at both sides of the assay site, so that the porous membrane can be dried.

In the bio-disc according to the present invention, the fluid movement may be controlled by a centrifugal force due to rotation of the bio-disc and opening and closing of the valve. However, in a case where the substrate in the assay site is a porous membrane, a coupling of an analyzed material and a probe is formed by diffusion of a reaction solution into the porous membrane, and the diffusion rate is determined based on a pore size of the porous membrane. If the reaction solution is moved by the centrifugal force generated from the rotation of the disc, the diffusion rates changes, so that it is difficult to obtain consistent reproducibility of the reaction of the analyzed material and the probe. In order to solve the aforementioned problems, according to the present invention, the before channel of the just-before valve of the assay site is constructed with a hydrophobic channel, the after channel is constructed with a hydrophilic channel, and the fluid movement into the assay site is performed by the opening of the just before valve and hydrophilic affinity of the hydrophilic channel and the reaction solution without using a centrifugal force. Since most of reaction solutions are hydrophilic, the reaction solution is remained in the hydrophobic chamber and channel before the opening of the just-before valve, and the reaction solution can flow into the assay site through the hydrophilic channel after the opening of the valve.

In the bio-disc according to the present invention, the bio material is at least one selected from DNA, oligo-nucleotide, RNA, PNA, ligand, receptor, antigen, antibody, and protein.

The chamber of the bio-disc according to the present invention may comprise at least one selected from the group consisting of: a preparation chamber for preparing a DNA sample from blood, cells, or RNA; a PCR chamber for amplifying the DNA sample through a polymerase chain reaction (PCR); a label chamber for reserving a label indicator; a hybridization chamber in which assay and diagnostic probes are arrayed on the substrate for hybridization with the amplified DNA from the PCR; and a trash chamber for collecting wastes generated from washing.

The preparation chamber of the bio-disc according to the present invention may reserve a lysis buffer solution used to destruct a cell and extract a DNA through lysis and particles or ferromagnetic beads having affinity to the extracted DNA. The particles may be silica or micro-bead coated with a DNA binding protein.

The preparation chamber may reserve only the buffer solution used to destruct the cell and extract the DNA without using the particles or ferromagnetic beads so as to prepare the DNA sample by using a centrifugal force generated from rotation of the bio-disc. More specifically, (1) cell membrane components including lipid is destructed by the lysis buffer solution, and the protein and the nucleic acid are dissolved. (2) When ethyl alcohol (ethanol) is applied, the DNA and RNA are extracted as a white precipitate. (3) When centrifugal separation is performed to obtain the DNA precipitated by ethanol, the DNA is collected at the end of the preparation chamber. After the valve of the preparation chamber toward the trash chamber is opened, the top layer solution is flowed into the trash chamber by rotation of the disc, so that the cell debris is separated and removed. Next, a dilution buffer is injected into the preparation chamber to be mixed with the DNA so as to increase a total volume of the DNA. The process (3) repeats about three times. (4) The connection valve toward the PCR chamber is opened, so that the DNA is moved into the PCR chamber.

The bio-disc according to the present invention may comprise a plurality of the PCR chambers. In this case, each PCR chamber may reserve one type or several types of primer. Alternatively, all the PCR chambers may reserve the same type of primer.

Alternatively, the chamber of the bio-disc according to the present invention may comprise at least one chamber selected from the group consisting of: a preparation chamber for preparing a serum sample, an antigen, or an antibody from blood or cells; an antigen-antibody reaction chamber in which immuno probes are arrayed on the substrate for an antigen-antibody reaction with the prepared antigen or antibody; and a trash chamber for collecting waste generated from washing. The serum sample may be a blood plasma sample.

In the preparation chamber of the bio-disc according to the present invention, a serum sample may be prepared by using a filter. Preferably, the serum sample may be prepared by using a centrifugal force generated by rotation of the disc. In this case, the preparation chamber may have a shape of a bottle having a depth to the outer circumference and a channel at a bottle neck separated by a predetermined height from the bottom to be connected to a next chamber. Therefore, a blood clot is collected on the bottom of the bottle, so that only the remaining serum can be moved to the next chamber.

In the bio-disc according to the present invention, the preparation chamber may be a chamber having a shape of a conical beaker, a flask, or a test tube in order to facilitate separating serum in centrifugal separation and a channel at a neck portion in order to be connected to a next chamber. In this case, due to a centrifugal force, a blood clot is collected in a circumferential outer space of the chamber (on a bottom of the conical beaker or the flask), so that the serum can be easily separated.

In the bio-disc according to the present invention, the chamber may further comprise a label chamber for reserving a labeled antibody. Here, the label may be a coloring particle linked with an antibody. The label may be gold, latex, a fluorescent material, an enzyme, and a radioactive isotope.

In the bio-disc according to the present invention, the immuno probe array may be constructed by arraying tumor markers on a substrate. More preferably, the immuno probe array may be constructed by arraying at least one tumor marker selected from AFP, PSA, CEA, CA19-9, CA125, and CA15-3 on the substrate.

In the bio-disc according to the present invention, the immuno probe may be at least one selected from myoglobin, CK-MB, and Troponin I (TnI) as a cardiac infraction marker and GS (Glutamine Synthetase) as an Alzheimer's disease marker.

In the bio-disc according to the present invention, the assay site may be analyzed by using any of conventional detection devices. Preferably, the assay site may be detected by a detection device coupled with a transforming device, and the detection device may include a light transmission type measuring device, an electro-chemical detection device, a capacitance and impedance measuring device, or an image sensor.

In the bio-disc according to the present invention, the light transmission type detection device may comprise: a laser device (light transmitting unit) which emits a laser beam onto a confined signal element and a released signal element; and an optical detector (light receiving unit) which detects a differential light transmission signal between the signal elements. The term "confined signal element" means that a signal such as a label is confined to the probe. The term "released signal element" means that a signal such as a label is released or cleaved from the probe. The optical transmission type detection device is distinguished from a conventional differential reflection type optical disc.

In the bio-disc according to the present invention, at least one optical detector (light receiving unit) may be arrayed and integrated along a circumference of the bio-disc to correspond to each assay site. Alternatively, at least one laser device (light transmitting unit) and at least one optical detector (light receiving unit) may be arrayed and integrated along a circumference of the bio-disc to correspond to each assay site.

In the bio-disc according to the present invention, the electro-chemical detection device and the capacitance and impedance measuring device may comprise: interdigitated array electrodes disposed on the substrate of the assay site; and an HRP (Horse Radish Peroxidase) and/or enzyme and/or a metal micro-sphere attached to the end of confined signal elements. In this case, the capacitance and impedance measuring device may be implemented by voltage generation, current detection, frequency generation, and oxidation reduction reaction. Detailed examples thereof are shown in FIGS. 9 to 11.

In the bio-disc according to the present invention, the interdigitated array electrodes may be constructed by coating a surface of a porous membrane with a conductive material. The conductive material may be gold or copper, and more preferably, gold. In comparison with a solid substrate, a surface area of the assay site can be increased, so that it is possible to greatly increase a sensitivity of interdigit.

In the bio-disc according to the present invention, the image sensor may be constructed with a CCD (charge coupled Device) sensor or a COMS sensor with or without a fluorescent filter to pick up an image of the label (coloring particle) linked with the probe in the assay site. The fluorescent filter may be optionally disposed in front of the sensor.

In the bio-disc according to the present invention, the assay site may comprise an immuno assay sector and a nucleic acid probe assay sector arranged in an angular or radial direction to enable an immuno assay and a nucleic acid probe assay to be performed concurrently.

The bio-disc according to the present invention may further comprise an impedance measuring device or an image sensor in the preparation chamber in order to detect a sample injection. The impedance measuring device may be an interdigitated array. The preparation chamber must be injected with a suitable amount of blood (or sample). A user must not operate the bio-disc without inserting blood. In order to prevent operation without blood, an image sensor may be used to observe the preparation chamber just before the start of the operation of the bio-disc and check whether or not a suitable amount of sample is injected into the preparation chamber.

In the bio-disc according to the present invention, the body of the bio-disc is constructed with an upper substrate, an intermediate substrate, and a lower substrate, and these substrates are adhered and assembled by using ultrasonic fusing, UV adhesive, or double-sided tape to form a single body. The positions of the hole and valves are determined according to the intermediate substrate.

The bio-disc according to the present invention may further comprise a memory or other storage means or RF IC for storing a protocol of the bio-disc, assay interpretive algorithms, standard control values for analysis, positional information on analysis sites, bioinformatics information, self-diagnostics information, bio-disc driver software, educational information for patients on clinical assays, a variety of web sites and links enabling a patient to communicate with a doctor or hospital at a remote location based on his/her diagnosis result, or encrypted personal information.

The bio-disc according to the present invention may further comprise statistic software and storage means for managing a history of the detection results of the assay site and provides periodical diagnosis information to a user. It is useful when the probe in the assay site is a tumor marker.

According to another aspect of the present invention, there is provided a bio-disc device comprising; the above-described bio-disc according to the present invention; a controller disc including a controller which supplies power or a control signal to the bio-disc; and an interfacing zone for connecting the bio-disc and the controller disc.

In the bio-disc device according to the present invention, the interfacing zone may comprise: a plurality of control signal nodes through which the control signal is supplied; and/or a power node through which power is supplied. Alternatively, the interfacing zone may comprise: grooves formed in the bio-disc and coated with a conductive material; and conductive arms protruding from the controller disc and engaging the grooves.

In the bio-disc device according to the present invention, the controller disc may be fixed to a turntable on which the bio-disc is mounted and further include an electromagnetic magnet or a movable permanent magnet for controlling a valve embedded in the bio-disc.

In the bio-disc device according to the present invention, the gap between the bio-disc and the controller disc may be in a range of from 0.1 mm to 2 mm. Due to the gap, it is possible to efficiently control the valve.

In the bio-disc device according to the present invention, power may be supplied to the controller disc through a brush or an electrical contact connected to an external power supply. In the specification, the term "brush" includes a conductive wire.

In the bio-disc device according to the present invention, the controller disc comprises an integrated circuit in a printed circuit board (PCB) or in a silicon wafer.

In the bio-disc device according to the present invention, the controller disc may further comprise a non-contact interface selected from among an infrared interface, an optical interface, and a wireless interface to transmit the result of a detection from the assay site by the detector to an external central control system, a storage unit, or an input output unit via the non-contact interface.

In the bio-disc device according to the present invention, the bio-disc and the controller disc may be integrated as a single body to form a controller disc-combined bio-disc. In this case, the controller disc-combined bio-disc has a monolithic circuit structure integrated into a silicon wafer via photolithography and etching processes, the monolithic circuit structure including the controller, the RF IC, a non-contact interface, an electrode plate or electromagnet for valve control, various circuit patterns, chambers, and channels.

According to another aspect of the present invention, there is provided a bio-disc driver apparatus comprising: a controller disc including a controller which supplies a power signal or a control signal to the bio-disc according to the present invention; a motor which rotates the controller disc and the bio-disc; a power supply unit which supplies power to the controller of the controller disc; an interface through which the control signal and/or the power signal are transmitted from the controller to the bio-disc; and a body which supports the bio-disc driver apparatus.

The bio-disc driver apparatus according to the present invention may further comprise a turntable on which the bio-disc is mounted, wherein the controller disc is fixed to the turntable and includes an electromagnetic magnet or a movable permanent magnet for controlling a valve embedded in the bio-disc In the bio-disc driver apparatus according to the present invention, the power supply unit supplies a positive power (+) to the controller disc by contact between an annular electrode and a brush and a negative power (−) to the controller disc through an electrical connection to a grounded motor body or a grounded motor shaft.

The bio-disc driver apparatus according to the present invention may further comprise a detection device coupled with a transforming device including an image sensor for detecting the assay site.

In the bio-disc driver apparatus according to the present invention, the controller disc may further comprise non-contact means for transmitting a detection result of the assay site to an external central control system, a storage device, or an input output device or receiving a command from the central control system. The detection result of the assay site may be transmitted to an external computer through a remote communication network. In this case, remote diagnostics is possible.

In the bio-disc driver apparatus according to the present invention, a circuit board on which the central control system, the storage device, or the input output device is disposed may be connected and engaged with the bio-disc driver body, and the central control system rotates or stops a motor for rotating and stopping the bio-disc and the controller dis.

In the bio-disc driver apparatus according to the present invention, the input output device may be a USB (Universal Serial Bus) device or a device according to IEEE-1394, ATAPI or Internet communication standard.

The bio-disc driver apparatus according to the present invention may further comprise an optical pickup device for reading a general optical disc selected from a group consisting an audio CD, a CD-R, a game CD, and a DVD.

The bio-disc driver apparatus according to the present invention may further comprise a bio-disc detection unit for determining whether a disc currently loaded on the bio-disc driver apparatus is a bio-disc or a general optical disc selected from among an audio CD, a CD-R, a game CD, and a DVD.

In the bio-disc driver apparatus according to the present invention, an optical pickup device may read a groove pattern or a data pattern at a particular area on a surface of the bio-disc to allow the central control system to recognize that a disc currently loaded on the bio-disc driver is a bio-disc.

In the bio-disc driver apparatus according to the present invention, a central control system may determine whether a currently loaded disc is a bio-disc or a general optical disc selected from among an audio CD, a CD-R, a game CD, and a DVD; transmit information read from the general optical disc using the optical pickup to a storage or output unit, transmit to the optical pickup information to be written, or output various read/write control signals if the currently loaded disc is determined to be a general optical disc; and transmit various control signals for the bio-disc via a non-contact interface to the controller if the currently loaded disc is determined to be a bio-disc.

In the bio-disc driver apparatus according to the present invention, at the time of loading the bio-disc, a new loading of the bio-disc is transmitted to the central control system in a wireless manner through a non-contact interface or an RF IC on the bio-disc, so that the central control system recognizes that the disc loaded on the bio-disc driver is the bio-disc.

The bio-disc driver apparatus according to the present invention may send an eject message or a warning message to a user if a bio-disc into which a sample has not be injected is loaded.

In the bio-disc driver apparatus according to the present invention, when an eject (unloading) or a stop command is input to the bio-disc driver apparatus during assay or diagnosis, the bio-disc driver apparatus sends a warning message or requests a user's password while continuing assay and diagnosis. If the user enters the correct password, the bio-disc driver apparatus stops the assay or diagnosis and ejects the bio-disc.

The bio-disc driver apparatus according to the present invention, may further comprise a memory for storing information on how many times the bio-disc device has been used, its validation period, and kinds of diseases which can be diagnosed, so as to provide a user with the stored information on the bio-disc or the availability of the bio-disc every time when the bio-disc is loaded.

The bio-disc driver apparatus according to the present invention may comprise: a play and search button and a stop button for general optical discs; and a light emitting diode (LED) indicating that a bio-disc has been loaded.

The bio-disc driver apparatus according to the present invention may comprise a liquid crystal display or a monitor to display the status of progress in main processes performed in the bio-disc such as a sample preparation process, PCR, a hybridization, and an antigen-antibody reaction in percentages or as a bar graph or a pie graph.

In the bio-disc driver apparatus according to the present invention, the body which supports the bio-disc driver may allow bio-disc top loading or bio-disc front loading. In addition, the bio-disc driver may have a plurality of turn tables so as to load a plurality of the bio-discs in one time.

According to another aspect of the present invention, there is provided a nucleic acid assay method using the bio-disc according to the present invention, the method comprising: preparing a DNA sample from blood, cells, or RNA; amplifying the prepared DNA through polymerase chain reaction (PCR); hybridizing amplified DNA products from the PCR to the assay and diagnostic probe arrayed on the assay site; and detecting a result of hybridization reaction in the assay site by using a detection device coupled with a transforming device, wherein the detection device includes a light transmission type measuring device, an electro-chemical detection device, a capacitance or impedance measuring device, or an image sensor.

In the nucleic acid assay method according to the present invention, the preparing of the DNA sample may comprises: injecting blood via a sample inlet into the preparation chamber; performing incubation in the preparation chamber to allow particles or ferromagnetic bead in the preparation chamber to attract DNA extracted through cell lysis; fixing the particles or ferromagnetic bead and slowly rotating the bio-disc to wash out and flow the cell debris into the trash chamber; and separating the DNA from the particles or ferromagnetic beads or resuspending the DNA in a resuspension buffer.

Alternatively, the preparing of the DNA sample may include: injecting blood via a sample inlet into the preparation chamber; and separating the DNA extracted through cell lysis by centrifugation using rotation of the bio-disc. In an example, sodium dodecyl sulfate (SDS) may be injected as a reagent for cell lysis. The SDS is a surfactant such as a detergent. By doing so, membrane components including lipid is destructed, and protein and nucleic acid are dissolved. At this time, phenol may be injected as a reagent for deforming the protein. After that, by centrifugal separation, the nucleic acid including DNA and RNA can be obtained.

In the nucleic acid assay method according to the present invention, the amplifying of the prepared DNA sample through PCR may comprises: slowly rotating the bio-disc to allow the prepared DNA sample to flow into the PCR chamber; and repeating a PCR cycle several times using a heater and a thermo-sensor installed in the PCR chamber to amplify the DNA sample.

The nucleic acid assay method according to the present invention may further comprise, after the PCR process: slowly rotating the bio-disc to allow a DNAse to flow into the PCR chamber; and heating the PCR chamber at a high temperature to deactivate the DNAse and form single-stranded DNA fragments (denaturing process).

In the nucleic acid assay method according to the present invention, each PCR chamber may comprise a heater which is controlled independently from the heaters of the other PCR chambers (in independent incubation time) to form the DNA fragments having different lengths.

According to another aspect of the present invention, there is provided an immuno assay method using the bio-disc according to the present invention, the method comprising: high speed rotating the bio-disc to extract serum or an antigen from blood; introducing the extracted antigen into a label chamber and performing incubation in the chamber for 1-2 minutes to bind the antigen to labeled antibodies and form a label-antigen complex; moving the label-antigen complex into the assay site; and performing cultivation in the bio-disc in a stationary state to induce an antigen-antibody reaction between the label-antigen complex and the capture antibodies; and adding a washing buffer and washing the assay site.

In the immuno assay method according to the present invention, in the moving of the label-antigen complex or the DNA into the assay site, the label-antigen complex or the DNA is allow to flow in to a porous membrane of the assay site by opening a just-before valve of the assay site and using a hydrophilic affinity of a hydrophilic channel without a centrifugal force.

The immuno assay method according to the present invention may further comprise, after the performing cultivation to induce an antigen-antibody reaction or hybridization reaction between the label-antigen complex or the DNA and the capture antibodies on the porous membrane, drying the porous membrane by a high speed rotation of the disc. If the porous membrane is saturated, the washing buffer solution cannot be absorbed. Therefore, in order to absorb the washing buffer solution, the porous membrane needs to be dried.

The immuno assay method according to the present invention may further comprise, after the drying, moving a washing buffer by opening a just-before valve of the assay site and using a hydrophilic affinity of a hydrophilic channel and cleaning the assay site by using the washing buffer.

The immuno assay method according to the present invention may further comprise, after the cleaning, drying the porous membrane by a high speed rotation of the disc. The drying is performed by inflow and outflow of air through air holes formed at both surfaces of the assay site due to rotation of the disc.

The immuno assay method according to the present invention may further comprise picking up an image with the image sensor in order to detect a result of an antigen-antibody reaction in the assay site. The image sensor for picking up an image may be a general CCD (Charge Coupled Device) sensor or a CMOS(Complementary Metal-Oxide Semiconductor) sensor for picking up a coloring particle as a result of the antigen-antibody reaction.

The immuno assay method according to the present invention may further comprise performing remote transmission of the result of the antigen-antibody together with a questionnaire sheet to a specialist at a remote location.

BRIEF DESCRIPTION OF THE DRAWINGS

These and/or other aspects and advantages will become apparent and more readily appreciated from the following description of the embodiments, taken in conjunction with the accompanying drawings of which:

FIGS. 1 and 2 are cross-sectional views showing a valve device using a micro-bead disposed in a bio-disc;

DETAILED DESCRIPTION OF THE EMBODIMENTS

Figure 3:
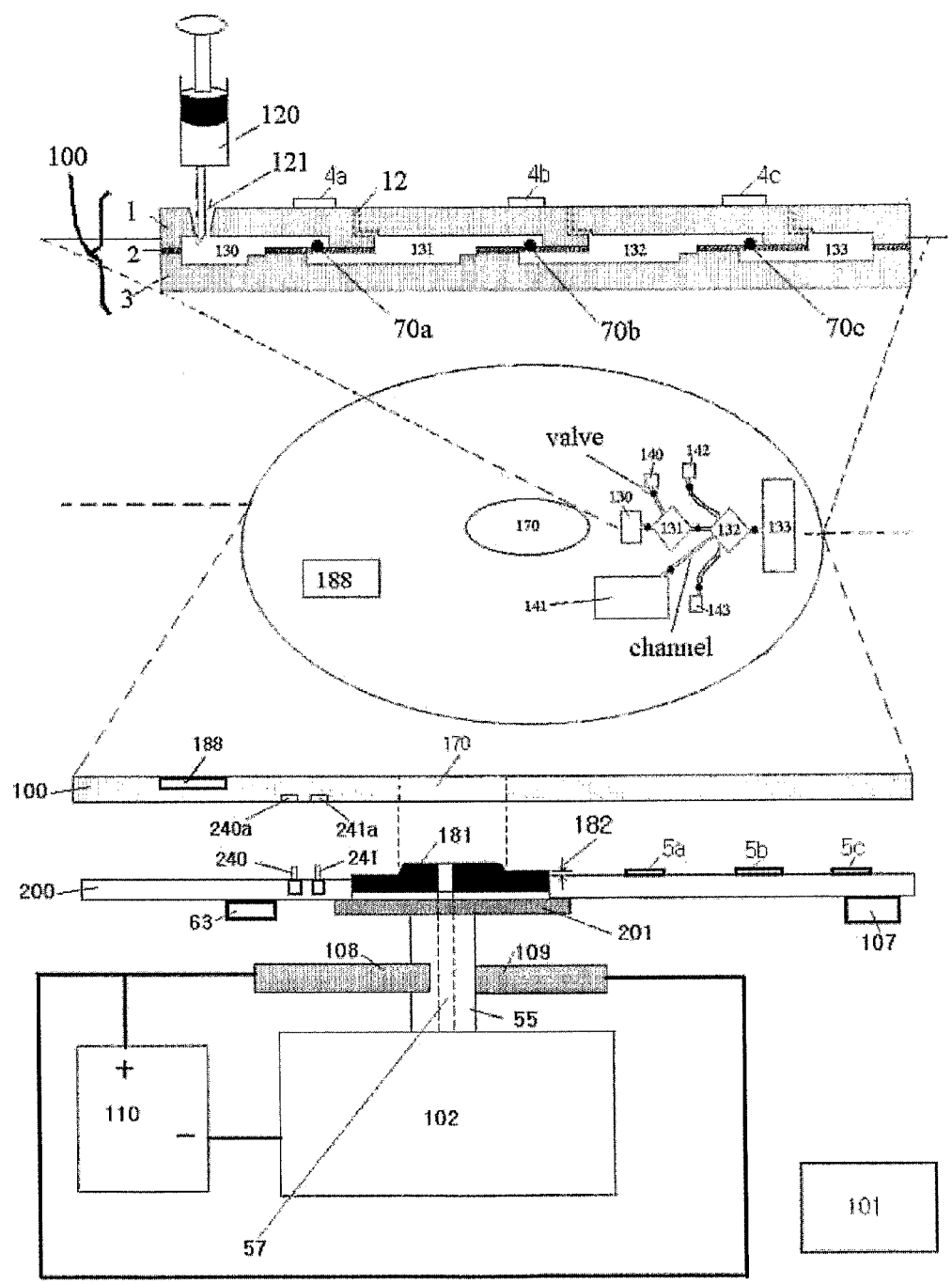
FIG. 3 is a view showing a bio-disc and a controller disc 200 for controlling the bio-disc according an embodiment of the present invention.

Reference will now be made in detail to the embodiments, examples of which are illustrated in the accompanying drawings, wherein like reference numerals refer to the like elements throughout. The embodiments are described below to explain the present invention by referring to the figures.

A bio-disc according to the present invention includes a valve which controls fluid flow or the flow rate in a lab-on-a-chip integrated in the bio-disc. The valve opens or closes a channel formed in the bio-disc using a microbead that is movable by the magnetic force generated by an electromagnet or a permanent magnet disposed on the top and/or bottom surface of the bio-disc. International Patent Application No. PCT/KR02/01035 filed 31 May 2002 and its priority Korean Application No. 10-2001-0031284 filed 31 May 2002, which are entitled "Micro valve apparatus using microbead and method for controlling the same", can be referred to for the detailed structure of the valve.

In exemplary embodiments of the bio-disc according to the present invention, the microbead may include, for example, a magnetic ball, ferroelectric particles, paramagnetic particles, diamagnetic particles, a stainless steel ball. Alternatively, the microbead may be made of a solid metal, plastic, or glass bead. When the microbead is made of a plastic or glass bead, the microbead is further coated with a metal or a cushion material. Solid metals for the microbead may be metal alloys. The microbead may be charged. In which case, instead of electromagnets, electrode plates are arranged on the top and bottom surfaces of the bio-disc. The microbead is charged and moved in the direction in which a voltage is applied to the electrode plates, to open or close a hole connecting channels in the lab-on-a-chip. The microbead has a diameter of 1 um-1 mm, preferably, 100 um-500 um. When the diameter of the microbead is larger, the hole can be opened or plugged with higher reliability due to an increase in the contact area between the hole and the microbead. The microbead may be a spherical permanent magnet or a film-like cylindrical or rectangular permanent magnet. The film-like permanent magnet may have a thickness of, preferably, 0.1 mm-0.5 mm. The electromagnet may be a wound wire having a diameter of, preferably, 0.01 mm-0.5 mm.

FIGS. 1 and 2 are sectional views of a bio-disc showing a valve apparatus therein using a permanent magnetic microbead 70a above which a permanent magnet 4a is disposed.

As shown in FIGS. 1 and 2, a bio-disc 100 includes an upper substrate 1, an intermediate substrate 2, and a lower substrate 3. Channels as flow paths, chambers as buffer reservoirs, and holes connecting the channels are formed in each of the upper, intermediate, and lower substrates 1, 2, and 3 by injection molding. Next, the upper, intermediate, and lower substrates 1, 2, and 3 are bound together to form a body of the bio-disc 100.

FIG. 1 illustrates a state where a hole 10 is plugged by a permanent magnetic microbead 70a to block a channel 16a. FIG. 2 illustrates a state where the permanent magnetic microbead 70a is removed from the hole 10 to interconnect the channel 16a. To plug the hole 10 with the permanent magnetic microbead 70a and block the channel 16a, as shown in FIG. 1, power is not applied to a electromagnet 5a or a movable permanent magnet 5a is removed from bottom surface of the bio-disc. In this case, the hole 10 is plugged by an attractive force between the micro-bead and a film-like permanent magnet 4a disposed above the micro-bead. In contrast, to open the hole 10 and interconnect the channel 16a, as shown in FIG. 2, power is applied to the electromagnet 5a such as to attract the permanent magnetic microbead 70a downward or the movable permanent magnet 5a is moved to bottom surface of the bio-disc.

Preferred examples of the lower magnet 5a include a film-like electromagnet with an air core and bobbinless coils or a movable permanent magnet. Since the bio-disc 100 according to the present invention includes the channel 16a, which is relatively narrow, as a fluid path, a ventilating hole 12 is formed in the upper substrate 1 to reduce the air pressure and allow a fluid to smoothly flow through the channel FIG. 3 illustrates a bio-disc 100, in which chambers as various assay buffer reservoirs and places for various reactions, channels as flow paths of a fluid sample and buffers, and valve apparatuses for controlling the opening and closing of the channels are integrated to form a lab-on-a-chip, a controller disc 200 for controlling the bio-disc 100 and bio driver apparatus including the controller disc 200.

Suitable materials for the bio-disc 100 according to the present invention include plastics, polymethylmethacrylate (PMMA), glass, mica, silica, any material for semiconductor wafers, etc. However, among these materials, plastics are most preferred for economical reasons and the convenience of processing. Suitable examples of plastics include polypropylenes, polyacrylates, polyvinyl alcohols, polyethylenes, polymethylmethacrylates, and polycarbonates, with polypropylenes and polycarbonates being preferred and polycarbonates being more preferred.

As described above with reference to FIGS. 1 and 2, the bio-disc 100 includes the upper substrate 1, the intermediate substrate 2, and the lower substrate 3. Channels as flow paths, chambers as buffer reservoirs, and holes connecting the channels are formed in each of the upper, intermediate, and lower substrates 1, 2, and 3 by injection molding. Next, the upper, intermediate, and lower substrates 1, 2, and 3 are bound together to form a body of the bio-disc 100.

International Patent Application No. PCT/KR02/01035 filed 31 May 2002 and its priority Korean Patent Application No. 10-2001-0031284 filed 31 May 2001, which are entitled "Micro valve apparatus using microbead and method for controlling the same", can be referred to for the detailed structure of the valve.

Suitable materials for the controller disc 200 include plastics, PMMA, glass, mica, silica, silicon, materials for printed circuit board (PCB), etc., in which PCB materials and any material for semiconductor wafers are preferred for their easy applicability in designing circuits.

The bio-disc 100 is built of the upper substrate 1, the intermediate substrate 2, and the lower substrate 3 stacked upon one another. Permanent magnetic microbeads 70a, 70b, and 70c are individually moved up and down by the magnetic force generated by respective upper permanent magnet and lower electromagnet pairs 4*a* and 5*a*, 4*b* and 5*b*, and 4*c* and 5*c* to close and open holes connecting channels. In FIG. 3, reference numeral 120 denotes a pipette or syringe for sample injection, reference numeral 121 denotes a sample inlet, and reference numeral 170 denotes a disk hole. Reference numeral 130 denotes a preparation chamber for preparing a DNA sample directly from blood or cells or from RNA through reverse transcription (RT) or for preparing a serum sample from blood, reference numeral 131 denotes a PCR chamber for polymerase chain reaction (PCR), and reference numeral 132 denotes a chamber for hybridization or antigen-antibody reaction, which is an assay site with capture probes for analyzing and diagnosing amplified DNA products from the PCR or with immuno arrays immobilized thereon. Reference numeral 133 denotes a trash chamber for collecting wastes generated during washing. Reference numeral 140 denotes a chamber for reserving a buffer for PCR, and reference numerals 141, 142, and 143 denote chambers for reserving various enzymes required for hybridization.

Opening and closing of the valve apparatuses at the start and ending points of time of each of the processes (preparation, PCR, hybridization, antigen-antibody reaction, and washing) are controlled by on/off control of the power supplied to the electromagnets 5*a*, 5*b*, and 5*c* mounted on the controller disc 200 and disposed below each of the permanent magnetic microbeads 70*a*, 70*b*, and 70*c*. Fluid flow in the bio-disc 100 is induced by the centrifugal force generated as it is rotated.

Reference numeral 55 denotes a rotary electrode coated with a conductive material, which is fixed to but electrically insulated with the axis of the motor 102. Reference numeral 110 denotes a power supply unit which supplies a direct current (DC) voltage and has a grounded negative port connected to the motor 102 and a positive port connected via brushes 108 and 109 to the rotary electrode 55 and supplies a positive voltage to the rotary electrode 55.

A positive voltage is supplied to the controller 63 and the wireless transmission and/or reception unit 107 of the controller disc 200 by frictional contact between the rotary electrode 55 and the brushes 108 and 109, whereas a negative voltage is supplied to the controller disc 200 via a motor shaft 57 connected to the motor 102 and an auxiliary substrate 201. Reference numerals 240 and 241 denote positive and negative power ports, respectively.

Reference numeral 181 denotes a turntable on which the bio-disc 100 or a general optical disc, such as an audio CD, a CD-R, a game CD, or a DVD, is loaded and which engages the disc hole 170 of the bio-disc 100 or a general optical disc. In disc 200 is fixed to the turntable 181, and the bio-disc 100 is loaded on the turntable 181 with a gap 182 of about 1 mm from the controller disc 200.

As described above, the memory embedded RFIC card 188 of the bio-disc 100 stores a protocol of the lab-on-chip, assay interpretive algorithms, standard control values for analysis, positional information on analysis sites, bioinformatics information, self-diagnostics, and the like. The RFIC card 188 may include bio-driver software, educational information for patients on clinical assays and may be adapted for users. The RFIC card 188 may include a variety of web sites and links, for example, a web site enabling a patient to communicate with a doctor or hospital based on his/her diagnosis result, and encrypted personal information to prevent unauthorized user assess.

A preferred example of the RFIC card 188 is a RAM or ROM embedded smart card. The information stored in the RFIC card 188 may be wirelessly transmitted to the central control system 101 to allow for remote analysis and diagnosis and encryption for personal information security.

Power nodes 240*a* and 241*a* of the bio-disc 100 are coated with a conductive material and are coupled with the respective power ports 240 and 241 of the controller disc 200, so that power is supplied to the bio-disc 100 from the controller disc 200.

Figure 4:
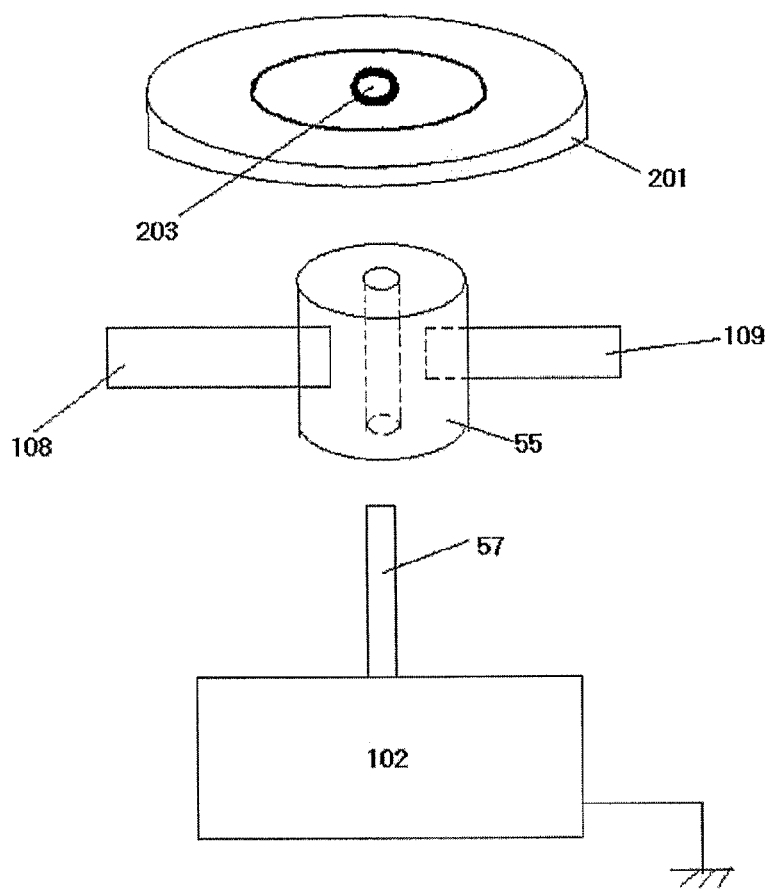
FIG. 4 is a view showing a connection portion for supplying power to the controller disc by using a frictional contact between a brush (or conducive wire) and an annular electrode according to an embodiment of the present invention.

FIG. 4 illustrates an example of the auxiliary substrate 201 which supplies the positive power generated by frictional contact between the brushes 108 and 109 and the rotary electrode 55, shown in FIG. 3 to the controller disc 200.

Referring to the motor 102 is grounded, and the motor shaft 57 connected to the motor 102 is also grounded. Accordingly, as the motor shaft 57 is inserted into a through (via) hole 203 of the auxiliary substrate 201, a negative voltage is supplied to the controller disc 200.

Figure 5:
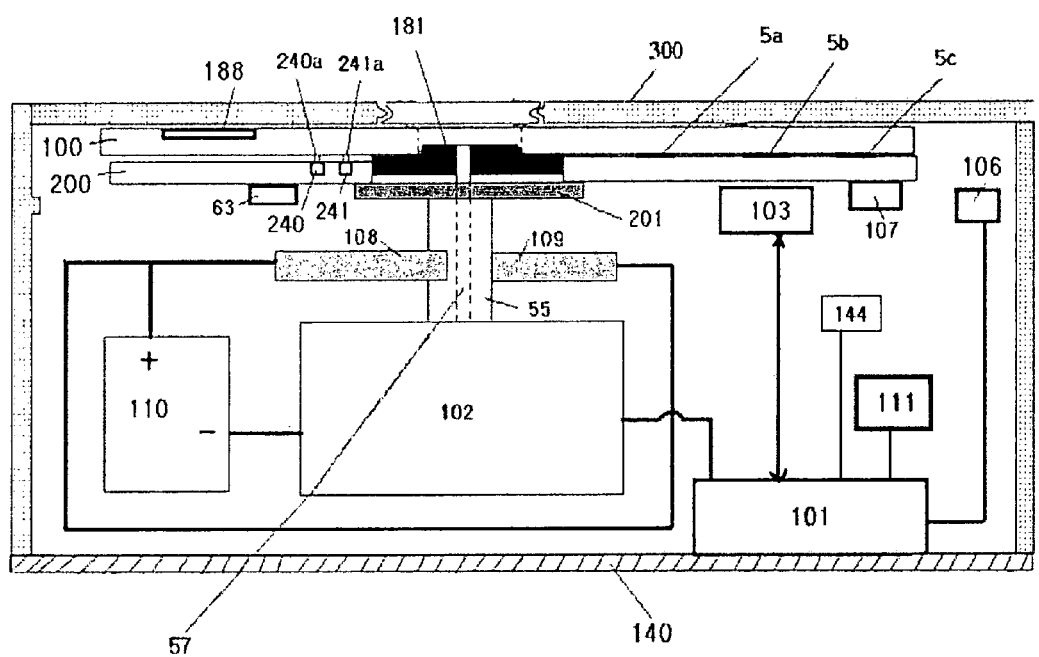
FIG. 5 is a view showing a bio-disc driver apparatus where a controller disc is embedded according to an embodiment of the present invention.

FIG. 5 illustrates an embodiment of a bio-driver apparatus assembled from the bio-disc 100 and the controller disc 200 of FIG. 3, in which the controller disc 200 is fixed to the turntable 181.

Positive and negative voltages on the controller disc 200 are supplied to the bio-disc 100 via power ports 240 and 241 of the controller disc 200. The positive and negative power ports 240 and 241 are connected with positive and negative voltages on the controller disc 200 and fit into the power nodes 240*a* and 241*a*, which are formed by coating with a conductive material, of the bio-disc 100 when the bio-disc 100 is loaded.

The bio-driver apparatus of FIG. 5 includes a power supply unit 110 for supplying power to the controller 63 of the controller disc 200 via the brushes 108 and 109. Reference numeral 300 denotes a body of the bio-driver apparatus. A printed circuit board (PCB) 140 is connected to the body 300 of the bio-driver apparatus as a base. A central control system 101 for controlling the bio-driver apparatus and a storage or input output unit 111 are arranged on the PCB 140. The central control system 101 controls a motor 102 to rotate the bio-disc 100 and the controller disc 200 or stop their rotation and controls the movement of an optical pickup 103.

The central control system 101 determines whether a disc currently loaded into the bio-driver apparatus is a general optical disc, for example, an audio CD, CD-R, a game CD, or a DVD, or a non-optical bio-disc. If the currently loaded disc is determined to be a general optical disc, the central control system 101 transmits information read from the optical disc using the optical pickup 103 to the storage or input output unit 111 or transmits information to be written to the optical pickup 103 and controls the operation of the optical disc using read/write control signals. If the currently loaded disc is determined to be a bio-disc, the central control system 101 sends various control signals for controlling the lab-on-a-chip of the bio-disc to the controller 63 of the controller disc 200 via non-contact interfaces 106 and 107 or the RFIC card 188 of the bio-disc 100.

The controller 63 of the controller disc 200 transmits the received control signals to the bio-disc 100 and controls the opening and closing of the valve apparatuses by on/off control of the power supplied to the electromagnet 5*a*, 5*b*, or 5*c* arranged on the controller disc 200. The electromagnet 5*a*, 5*b*, and 5*c* of the controller disc 200 is arranged so close to the bio-disc 100 that the repulsive or attractive force of the permanent magnetic microbeads 70*a*, 70*b*, and 70*c* reaches the electromagnet 4*a*, 4*b*, and 4*c*. The controller disc 200 fixed to the turntable 181 has a gap 182 of about 1 mm from the bio-disc 100 loaded on the turntable 181.

The bio-disc driver apparatus according to the present invention may further comprise a bio-disc detection unit for determining whether a disc currently loaded on the bio-disc driver apparatus is a bio-disc or a general optical disc selected from among an audio CD, a CD-R, a game CD, and a DVD.

In the bio-disc driver apparatus according to the present invention, an optical pickup device may read a groove pattern or a data pattern at a particular area on a surface of the bio-disc to allow the central control system to recognize that a disc currently loaded on the bio-disc driver is a bio-disc. Alternatively, when a bio-disc is loaded, a non-contact interface or a RFIC card on the bio-disc may wirelessly transmit the loading information to the central control system to allow the central control system to recognize that a disc currently loaded on the bio-disc driver is a bio-disc.

As described above, the non-contact interfaces 106 and 107 are reception and/or transmission units for non-contact interfacing.

The controller 63 transmits the result of a detection from the array chamber (assay site) 132 of the bio-disc 100 by a detector including an optical device, a non-optical device, an electrochemical device, or a capacitance and impedance measurement device, via the non-contact interfaces 106 and 107, which may be implemented with an infrared interface, optical interface, or wireless interface, to the central control system 101 or the storage or input output unit 111. Alternatively, the controller 63 transmits the result of a detection from the array chamber (assay site) 132 of the bio-disc 100 by a detector including an optical device, a non-optical device, an electrochemical device, or a capacitance and impedance measurement device, via the RFIC card 188 and a wireless transmission/reception unit (not shown), to the central control system 101 or the storage or input output unit 111. Alternatively, an image sensor 144 arranged on the PCB 140 transmits the results of a detection from the assay site 132 by the image sensor to the central control system 101 or the storage or input output unit 111.

Figure 6:
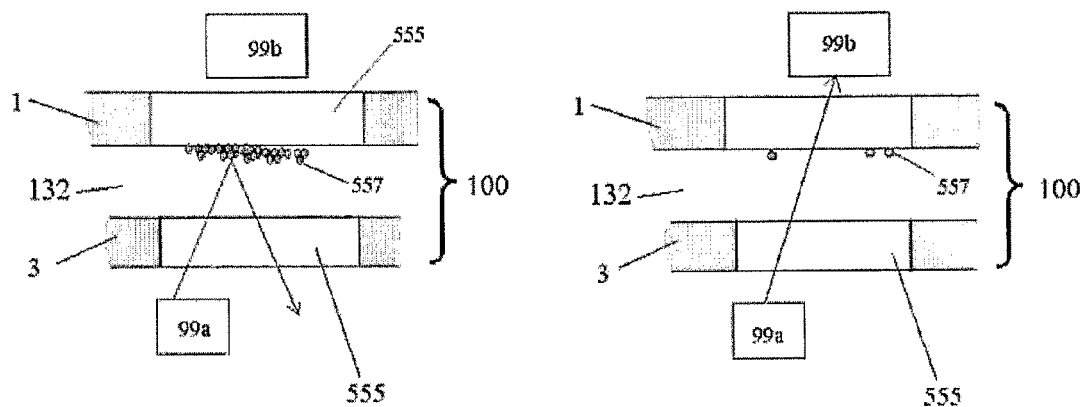
FIGS. 6 to 8 are views showing optical measuring devices according to embodiments of the present invention.

FIG. 6 illustrates an embodiment of the optical assay detectors which detect analyte-specific signals from the assay site 132 using light transmission through metal microspheres.

The left sectional view of FIG. 6 shows a state where numerous signal elements 557 are immobilized on the surface of the upper substrate 1 of the bio-disc 100 (confined signal element), and the right sectional view of FIG. 6 shows a state where only a few signal elements 557 remain on the upper substrate 1 after cleavage reaction (released signal element).

In the embodiment of FIG. 6, the optical array detectors 99a and 99b are implemented with a laser device (light transmitting unit), which emits a laser beam onto the cleavable signal elements 557, and a photodetector (light receiving unit), which detects a differential light transmission signal. A transparent opening 555 is further formed for higher sensitivity of the photodetector 99b.

Figure 7:
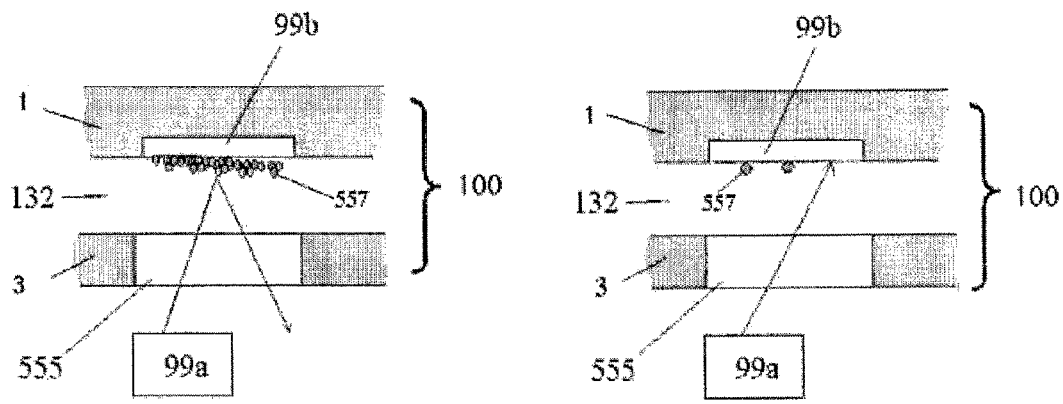

FIG. 7 illustrates a modification of the optical array detectors of FIG. 6 based on light transmission, in which the photodetector 99b is integrated into the upper substrate 1. In this embodiment, a plurality of photodetectors 99b are arrayed one-to-one corresponding to a plurality of assay sites. This arrangement of the plurality of photodetectors 99b is distinguished from a modular light transmission and reception unit used in the general optical pickup 103, the modular light transmission and reception unit causing a low sensitivity problem at a receiving site due to its longer reflection path.

Figure 8:
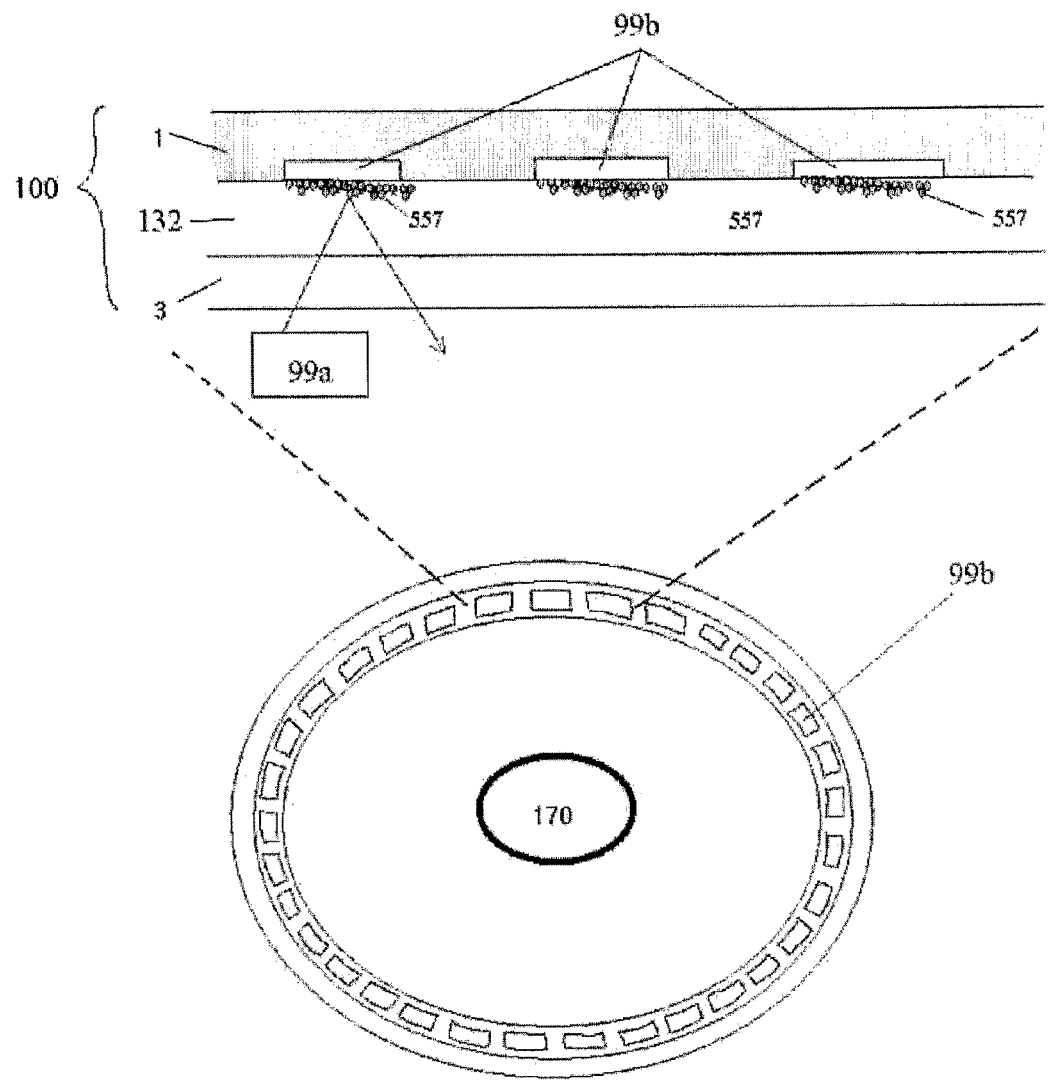

FIG. 8 illustrates an embodiment of a bio-disc with a plurality of photodetectors 99b arrayed along its outer perimeter region. As the bio-disc is rotated, individual analyte sites in the bio-disc are sequentially detected by the corresponding photodetectors 99b.

FIGS. 9 through 13 illustrate examples of electrochemical detectors or capacitance and impedance measurement devices for detecting analyte-specific signals from the assay site 132 of the bio-disc 100. Some of the electrochemical detectors or capacitance impedance measurement devices illustrated in FIGS. 9 through 13 are implemented with interdigitated array electrodes 702 and 703 arranged on a substrate 701 and a metal microsphere 40 or horse radish peroxidase (HRP) 41 attached as signal responsive moiety to each end of probes on the substrate 701. Some of the electrochemical detectors or capacitance impedance measurement devices are based on antigen-antibody reaction mainly used for immunochromatography. In the bio-disc according to the present invention, the porous membrane may be any membrane having a large number of pores. The substrate 701 may be preferably a porous membrane coated with interdigitated array electrodes and the porous membrane may be one selected from NC (nitrocellose) membrane, a nylon membrane, and aligned nanotubes.

Figure 9:
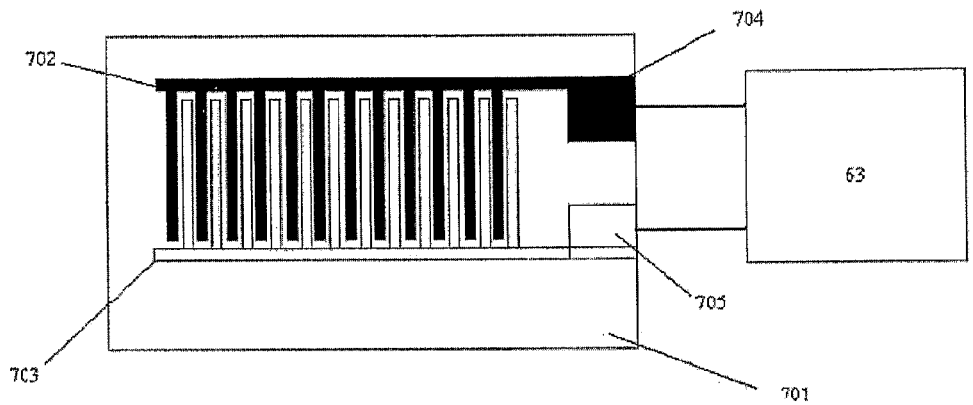
FIGS. 9 to 14 are views showing detection method using an electro-chemical detection device, a capacitance and impedance measuring device, or an image sensor according to an embodiment of the present invention.

FIG. 9 illustrates an example of an electrochemical detector or a capacitance and impedance measurement device with interdigitated array electrodes 702 and 703.

The controller 63 applies an AC signal having a given bandwidth to two input ports 704 and 705 of the respective interdigitated array electrodes 702 and 703 to measure the frequency response characteristics of assay sites and then the capacitance and impedance of the assay sites from the frequency response characteristics. Alternatively, the controller 63 may be able to measure a voltage or a current induced as a result of the reduction/oxidation (REDOX) of analytes by HRP in $H_2O_2$ solution, thereby enabling electrochemical detection of assay sites. For the detailed structure of such a capacitance and impedance measurement device using interdigitated array electrodes, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides," can be referred to.

Figure 10:
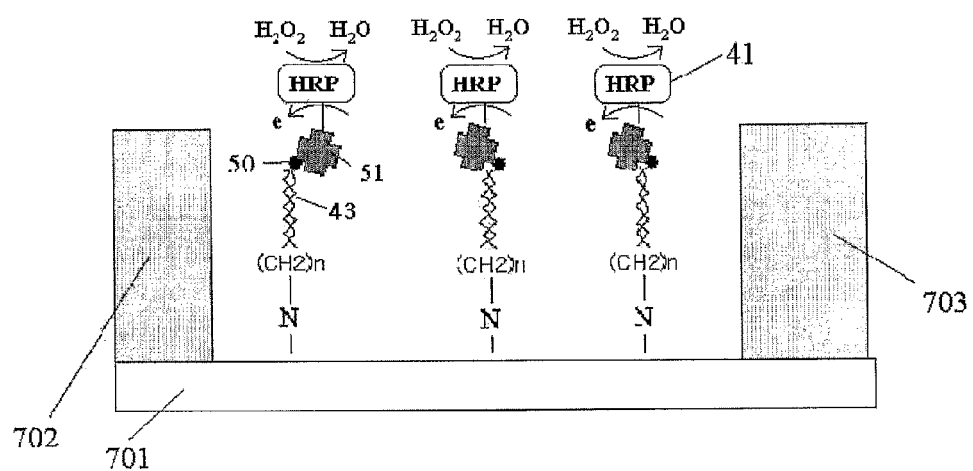
Figure 11:
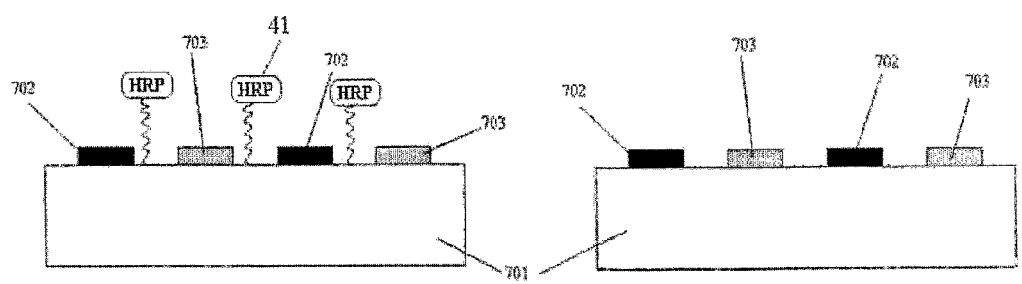

FIGS. 10 and 11 illustrate an example of an electrochemical detector or a capacitance and impedance measurement device for detecting analyte-specific signals from the assay site 132 of the bio-disc 100. The electrochemical detector or the capacitance and impedance measurement device of FIGS. 10 and 11 is implemented with the interdigitated array electrodes 702 and 703 arranged on the substrate 701 and HRP 41 attached as signal responsive moiety to each cleavable signal element immobilized as a probe on the substrate 701. Electrons are generated as a result of successive REDOX reactions by the HRP 41 and induce a current and a voltage across the interdigitated array electrodes 702 and 703. The sensitivity of the interdigitated array electrodes 702 and 703 becomes higher with more digits.

The assay site 132 of the bio-disc 100 is manufactured by aminating the surface of the substrate 701, forming a nonreactive monolayer, for example, of alkane chains the aminated surface of the substrate 701, and immobilizing cleavable signal elements labeled with biotin 50, wherein the nonreactive layer is for preventing direct contact of the cleavable signal elements with the substrate 701.

After sample injection, cleavable signal elements which are not hybridized with a sample remain as single strands are cleaved by a and removed through washing. Meanwhile, cleavable signal elements which are hybridized with the sample and form double strands 43 remain after the cleavage and washing processes. Next, streptavidin-labeled HRP is injected to bind the streptavidin 51 to the biotin labeled to the signal elements.

Next, a series of REDOX reactions of the signal elements are caused by the HRP in $H_2O_2$ solution to induce a voltage and a current across the interdigitated array electrodes 702 and 703. The controller 63 measures the voltage and the current across the interdigitated array electrodes 702 and 703. In this way, a differential electrochemical signal between the confined and cleaved (released) signal elements can be detected.

The left sectional view of FIG. 11 shows a state where cleavable signal elements remain on the bio-disc 100, so that the signal elements in the assay site 132 are highly likely to be oxidized and reduced by the HRP in solution. The right sectional view of FIG. 11 shows a state where most cleavable signal elements are cleaved and removed through washing so that REDOX reaction is unlikely to occur. A differential electrochemical signal between the two states is detected.

Figure 12:
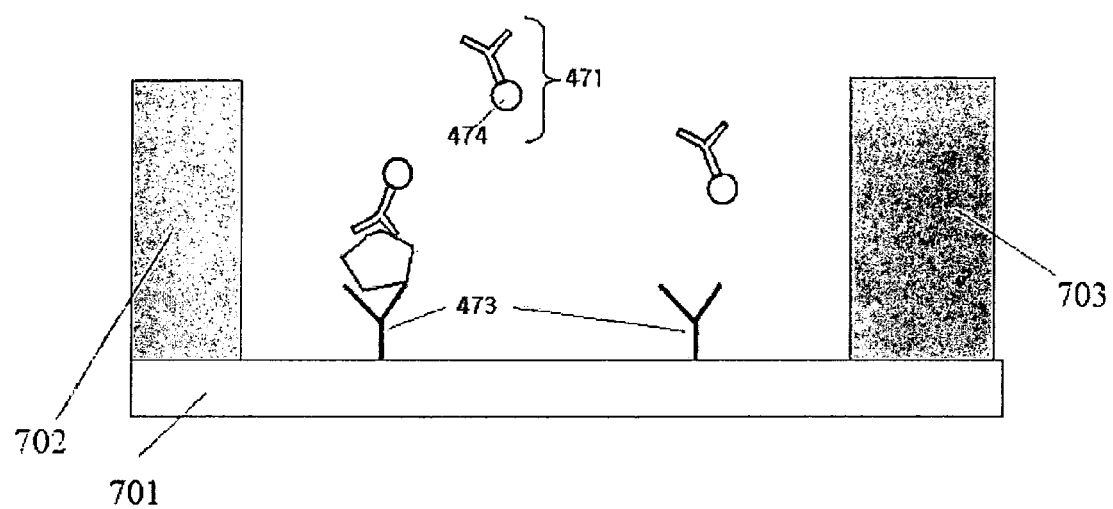

FIG. 12 illustrates another example of an electrochemical detector or a capacitance and impedance measurement device for detecting analyte-specific signals from the assay site 132 of the bio-disc 100. The electrochemical detector or the capacitance and impedance measurement device of FIG. 12 is implemented with the interdigitated array electrodes 702 and 703 arranged on the substrate 701 and a labeled antibody 471 which forms a label-antigen complex with a target sample (analyte or antigen) to be assayed. The label-antigen complex is applied to an assay site 132 in which capture antibodies 473 are immobilized on the substrate 701. The electrochemical detector or the capacitance and impedance measurement device of FIG. 12 is based on antigen-antibody reaction between the label-antigen complex and the capture body 473. The labeled antibody 471 is labeled with coloring moiety 474 made of, preferably, gold, latex, a fluorescent material, an enzyme, or a radioactive isotope.

Figure 13:
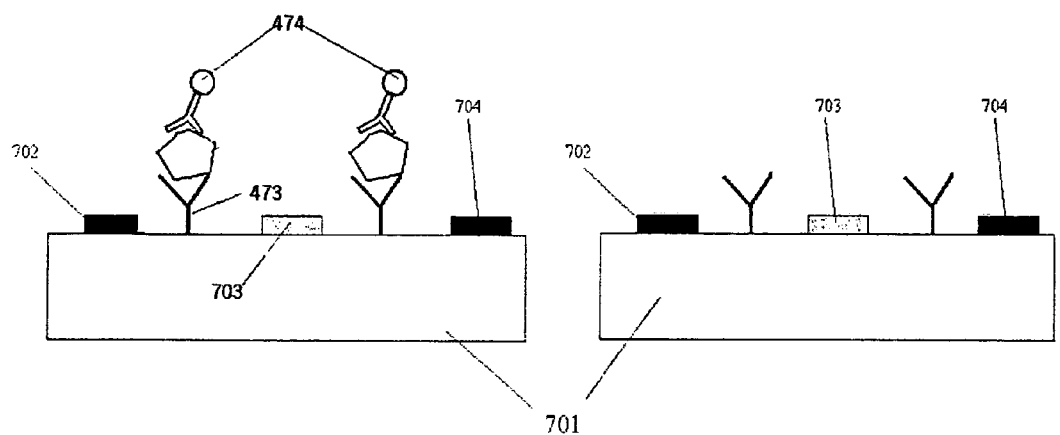

The left sectional view of FIG. 13 shows a state where the signal elements labeled with gold, latex, a fluorescent material, an enzyme, or a radioactive isotope, which are products of antigen-antibody reactions in the bio-disc 100, remain on the substrate 701 after washing. The right sectional view of FIG. 13 shows a state where no antigen-antibody reaction takes place and only the capture antibody remains unreacted after washing. A differential capacitance and impedance signal between the two states is detected.

Figure 14:
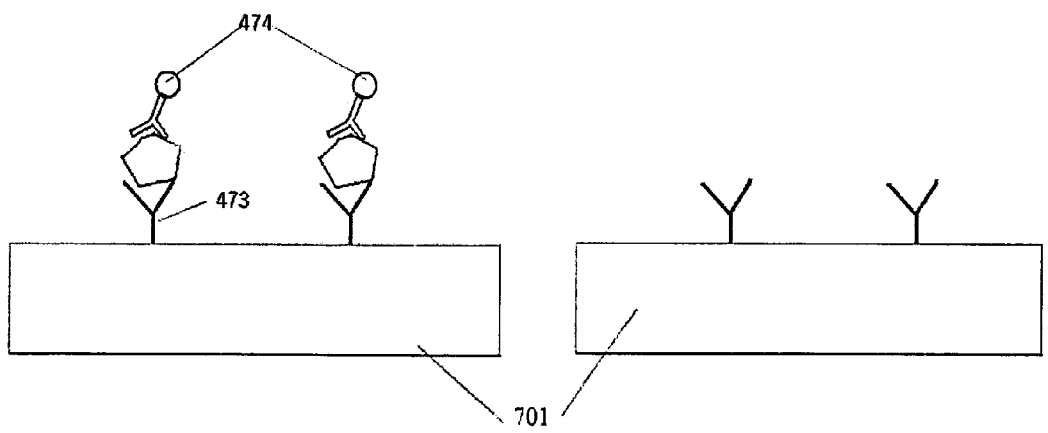

FIG. 14 illustrates an image sensor for detecting analyte-specific signals from the assay site 132 of the bio-disc 100. The label-antigen complex is applied to an assay site 132 in which capture antibodies 473 are immobilized on the substrate 701. The image sensor obtains coloring information based on antigen-antibody reaction between the label-antigen complex and the capture antibody 473. The labeled antibody 471 is labeled with coloring moiety 474 made of, preferably, gold, latex, a fluorescent material, an enzyme, or a radioactive isotope. The substrate 701 may be preferably a porous membrane which may be one selected from NC (nitrocellose) membrane, a nylon membrane, and aligned nanotubes.

When the label-antigen complex reacts with the capture antibody 473, the antigen-antibody reaction product remains as a confined signal element after washing. When the label-antigen complex does not react with the capture antibody 473, the capture antibody 473, which remains unreacted, serves as a released signal element. The left sectional view of FIG. 14 shows a state where the signal elements labeled with gold, latex, a fluorescent material, an enzyme, or a radioactive isotope, which are products of antigen-antibody reactions in the bio-disc 100, remain on the substrate 701 after washing. The right sectional view of FIG. 14 shows a state where no antigen-antibody reaction takes place and only the capture antibody remains unreacted after washing. A differential coloring information between the two states is detected by the image sensor.

Figure 15:
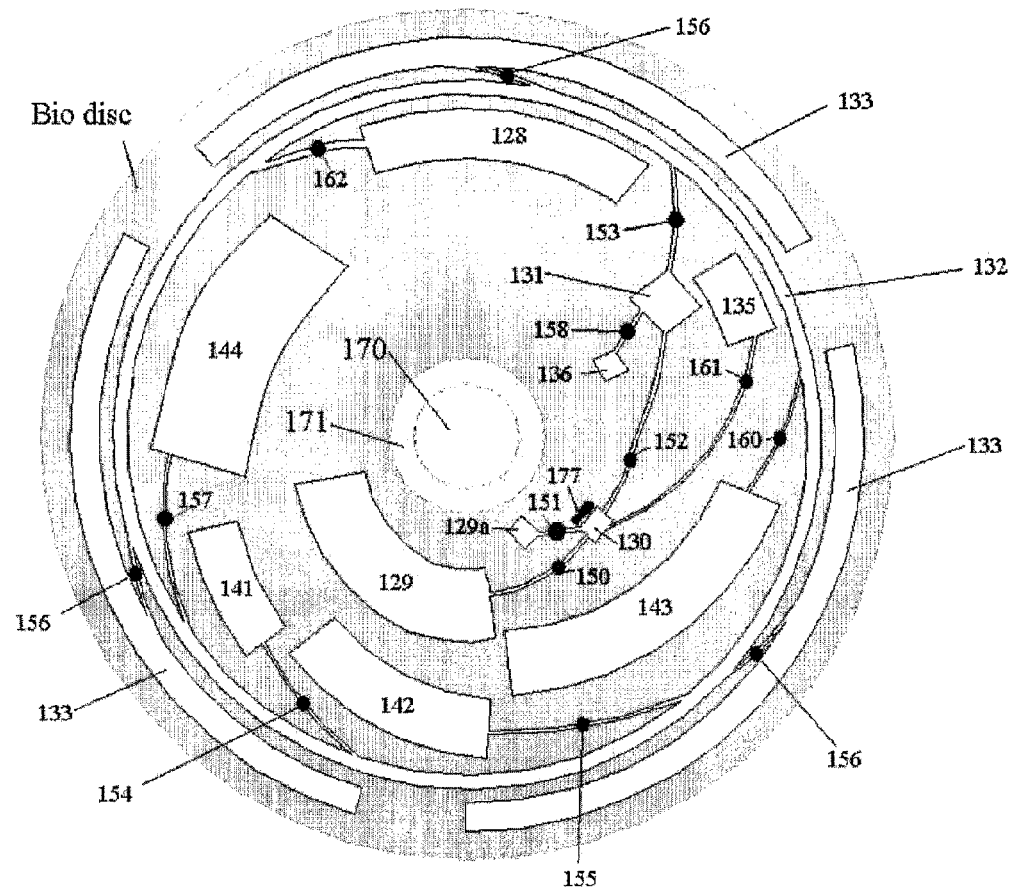
FIGS. 15 to 20 are views showing a bio-disc according to an embodiment of the present invention.
Figure 16:
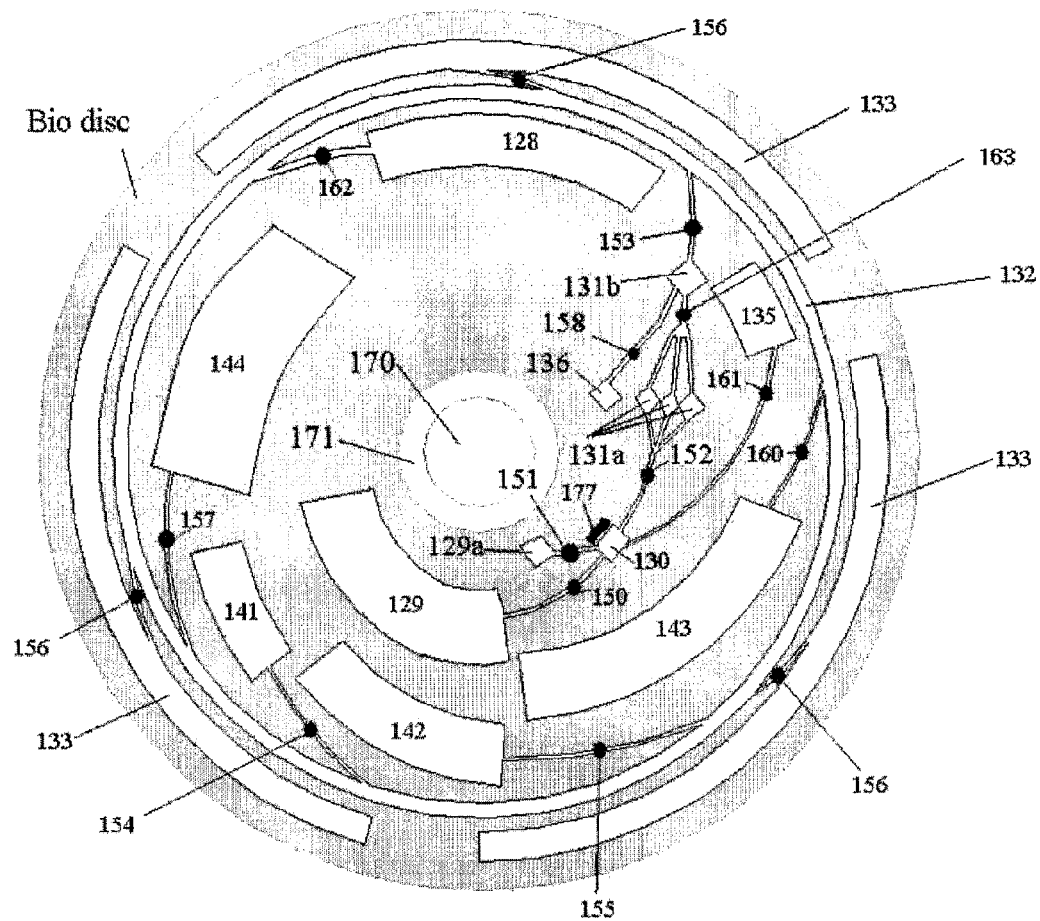

Embodiments of bio-discs according to the present invention are illustrated in FIGS. 15 through 18. FIGS. 15 and 16 illustrate various examples of labs-on-a-chip for nucleic acid assay which can be integrated into the bio-disc 100 according to the present invention.

In FIGS. 15 and 16, reference numeral 170 denotes a disc hole, and reference numeral 171 denotes an interfacing zone for electrical connection with the controller disc 200. Reference numeral 130 denotes a preparation chamber for preparing a DNA sample or a serum sample from blood, cells, or RNA; reference numerals 131 and 131*a* denote PCR chambers for polymerase chain reaction (PCR), in which a buffer containing various enzymes, such as polymerase, dNTPs and primers, is reserved; reference numeral 132 denotes a chamber for hybridization, which is an assay site with biotin-labeled capture probes for analyzing and diagnosing amplified DNA products from the PCR; and reference numeral 133 denotes a trash chamber for collecting wastes generated during washing.

The chambers for the main processes, such as sample preparation, PCR, hybridization, and washing, are arranged in a spiral formation from the center to the outer perimeter and are interconnected with each other, so as to induce natural fluid flow by centrifugal force to allow for sequential processes. In addition, reagent reservoir chambers are arranged in a spiral formation near the corresponding reaction chambers.

Reference numeral 129 denotes a washing buffer reservoir; reference numeral 129*a* denotes a distilled water reservoir; reference numeral 144 denotes a hybridization buffer reservoir; reference numeral 136 denotes a reservoir of a DNAse used in DNA fragmentation into appropriate size; and reference numerals 141, 142, and 143 denote reservoirs of various enzymes used in hybridization. Reference numeral 141 denotes a reservoir of a used in single strand cleavage; reference numeral 142 denotes a reservoir of streptavidin-labeled metal microspheres; and reference numeral 143 denotes a reservoir of phosphate buffered saline (PBS).

Reference numerals 150, 151, 152, 153, 154, 156, 157, 158, 160, 161, 162, and 163 denote valves. Fluid flow in the bio-disc 100 is controlled by the centrifugal force generated as the bio-disc is rotated and by opening and closing the valves. Reference numeral 177 denotes an electromagnet or a permanent magnet embedded in the bio-disc 100, which may be moved above or below the preparation chamber 130, instead of be embedded in the bio-disc 100, when a magnetic power is needed.

Opening and closing of the valves at the start and ending points of time of each of the main processes, including sample preparation, PCR, hybridization, and washing, are performed by controlling the balance between the following two forces: an attractive force between the micro-bead and a permanent magnet disposed above the micro-bead and a magnetic force between the micro-bead and an electromagnetic or movable permanent magnet disposed under the micro bead.

In other words, opening and closing of the valves at the start and ending points of time of each of the main processes, including sample preparation, PCR, hybridization, and washing, are controlled by controlling the on/off of the power applied to the electromagnets arranged below each film-like cylindrical permanent magnet of the valves or the mechanical movement of the movable permanent magnet arranged below the film-like cylindrical permanent magnet of the valves In case of controlling the on/off of the power applied to the electromagnets, the on of power make the valves opened by an attractive force between the film-like cylindrical permanent magnet and the electromagents disposed under the film-like cylindrical permanent magnet, and the off of the power make the valves closed by an attractive force between the film-like cylindrical permanent magnet and a permanent magnet disposed above the film-like cylindrical permanent magnet.

In case of controlling the mechanical movement of the movable permanent magnet, the approach movement of the movable permanent magnet make the valves opened by an attractive force between the film-like cylindrical permanent magnet and the movable permanent magnet disposed under the film-like cylindrical permanent magnet, and the release movement of the movable permanent magnet make the valves closed by an attractive force between the film-like cylindrical permanent magnet and a permanent magnet disposed above the film-like cylindrical permanent magnet.

Reference numeral 128 denotes a distilled water reservoir, and reference numeral 135 denotes a trash chamber.

FIG. 15 illustrates an embodiment of a bio-disc including one PCR chamber in its lab-on-a-chip. FIG. 16 illustrates an embodiment of a bio-disc including a plurality of PCR chambers in its lab-on-a-chip. In the structure of FIG. 16, each PCR chamber reserves one type of primer. Alternatively, all of the PCR chambers reserves the same type of primer. The amplified DNA products from each of the PCR chambers combine in a chamber 131*b*.

Figure 17:
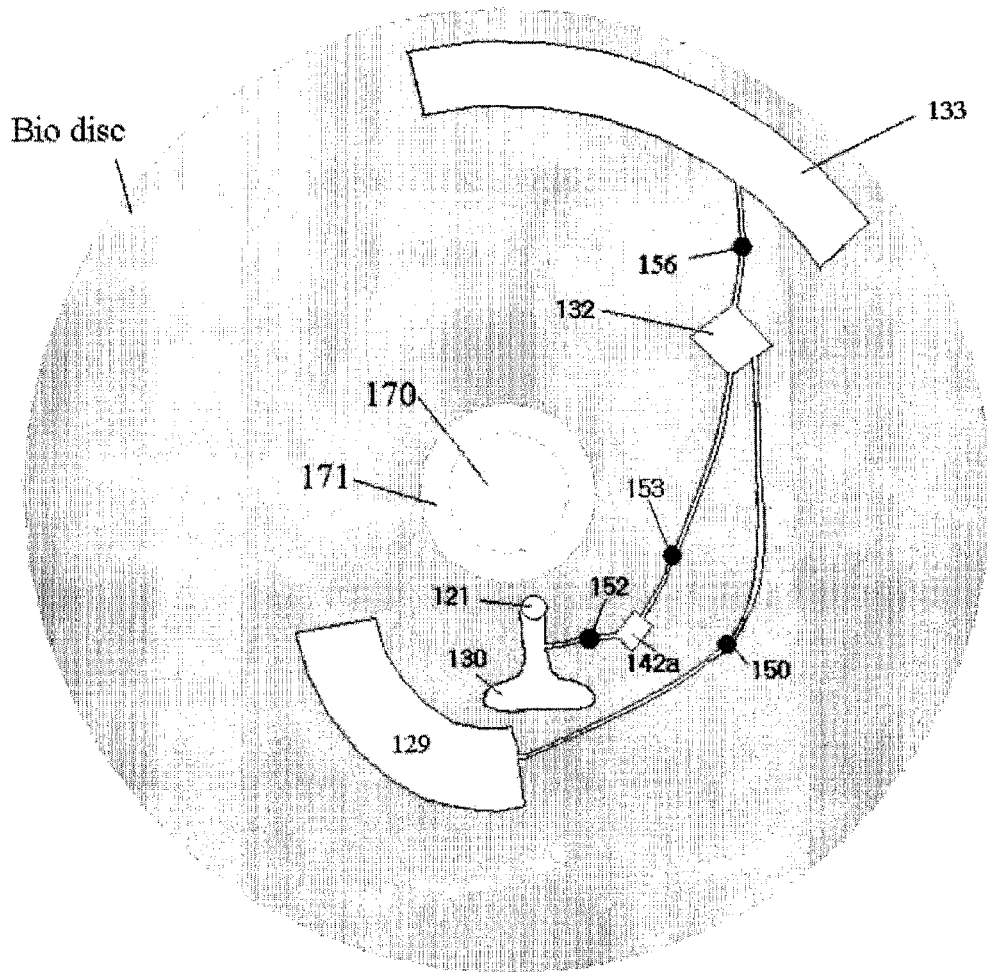
Figure 18:
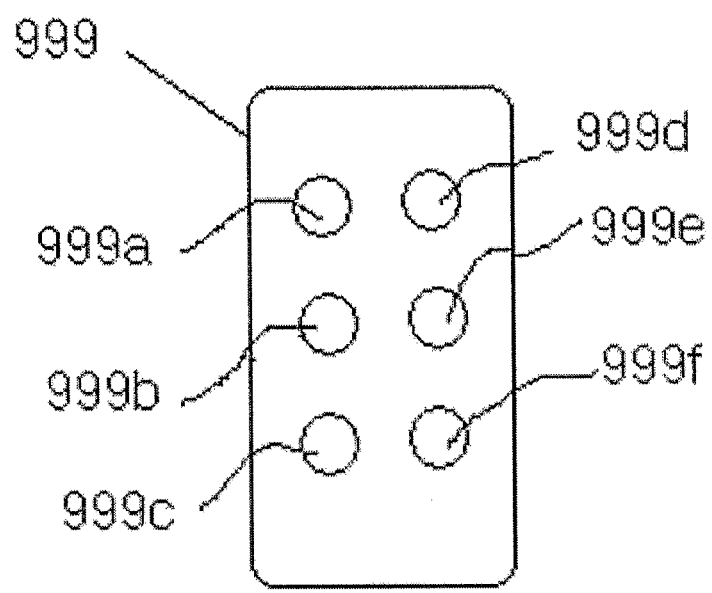

FIG. 17 illustrates an embodiment of a lab-on-a-chip designed for antigen-antibody reaction, which can be integrated into the bio-disc 100. FIG. 18 illustrates an embodiment of an array in the assay site 132 of FIG. 17. In FIG. 17, reference numeral 130 denotes a preparation chamber for preparing a serum sample from blood injected via a sample inlet 121; reference numeral 132 denotes a chamber for antigen-antibody reaction, which is an assay site with immuno arrays immobilized thereon so as to analyze and diagnose an antigen, i.e., sample or analyte; and reference numeral 133 denotes a trash chamber for collecting wastes generated during washing. The assay site 132 may be constructed by fixing the capture antibodies between the interdigitated array electrodes coated on a porous membrane or on the porous membrane without the interdigitated array electrodes. The porous membrane may be one selected from NC (nitrocellose) membrane, a nylon membrane, and aligned nanotubes.

The chambers for the main processes, such as sample preparation, antigen-antibody reaction, and washing, are arranged in a spiral formation from the center to the outer perimeter of the disc and are interconnected with each other, so as to induce natural fluid flow by centrifugal force to allow for sequential processes. In addition, reagent reservoir chambers are arranged in a spiral formation near the corresponding reaction chambers.

Reference numeral 129 denotes a washing or elution buffer reservoir, and reference numeral 142*a* denotes a labeled antibody reservoir. labeled antibodies in reservoir 142*a* are labeled with coloring moiety made of, for example, gold, latex, a fluorescent material, an enzyme, or a radioactive isotope. Reference numerals 150, 152,153, and 156 denote valves. Fluid flow in the bio-disc 100 is controlled by the centrifugal force generated as the bio-disc is rotated and by opening and closing the valves.

Preferably, the serum sample may be prepared by using a centrifugal force generated by rotation of the disc. In this case, the preparation chamber may have a shape of a conical beaker or a flask in order to facilitate separating serum in centrifugal separation and a channel at a neck portion in order to be connected to a next chamber. Therefore, when a centrifugal force is applied, a blood clot is collected in a circumferential outer space of the chamber and a serum is collected in a circumferential inner space of the chamber, so that the serum can be easily separated because the serum layer is relatively high compared to the blood clot layer. Next, the serum can be moved to the next chamber by slowly rotating the bio disc while opening the valve 152.

The assay site 132 may be constructed by fixing the capture antibodies between the interdigitated array electrodes coated on a porous membrane or on the porous membrane without the interdigitated array electrodes. The porous membrane may be one selected from NC (nitrocellose) membrane, a nylon membrane, and aligned nanotubes.

In the bio-disc of FIG. 17, the immuno probe array may be constructed by arraying tumor markers as a capture antibody on a substrate. More preferably, the immuno probe array may be constructed by arraying at least one tumor marker selected from AFP, PSA, CEA, CA19-9, CA125, and CA15-3 on the substrate. Further, the immuno probe array may be constructed by arraying at least one selected from myoglobin, CK-MB, and Troponin I (TnI) as a cardiac infraction marker and GS (Glutamine Synthetase) as an Alzheimer's disease marker.

Generally, in the initial state of cancer, the blood concentration of the tumor marker is not high and in a normal range. As the cancer being developed, the blood concentration of the tumor marker is increased and positively detected. In this concern, The bio-disc according to the present invention may further comprise statistic software and storage means for managing a history of the detection results of the assay site and provides periodical diagnosis information to a user In the bio-disc 100, the fluid movement may be controlled by a centrifugal force due to rotation of the bio-disc and opening and closing of the valve; a centrifugal force due to rotation of the bio-disc and hydrophilic affinity of the hydrophilic channel and opening and closing of the valve; or a centrifugal force due to rotation of the bio-disc and hydrophilic affinity of the hydrophilic channel with rapid and repeative opening and closing of the valve. For the fluid movement to the hydrophilic channel, an initial resistance which is generated at the interface between hydrophobic coating and hydrophilic coating should be overcome. The rapid and repeative opening and closing of the valve induce a shaking in the fluid and help the fluid movement to overcome the initial resistance. After the resistance is overcome, the fluid can be moved into the hydrophilic channel by hydrophilic affinity.

FIG. 18 illustrates an embodiment of the assay site in which the tumor markers are arrayed in spots on the substrate such as the porous membrane 999 or polycarbonate. In this example, 6 tumor markers, AFP (999*a*), PSA (999*b*), CEA (999*c*), CA19-9 (999*d*), CA125 (999*e*), and CA15-3 (999*f*) are arrayed on the porous membrane 999. For the detailed descriptions on the method for fixing the antibody on the polycarbonate, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides," can be referred to.

Figure 19:
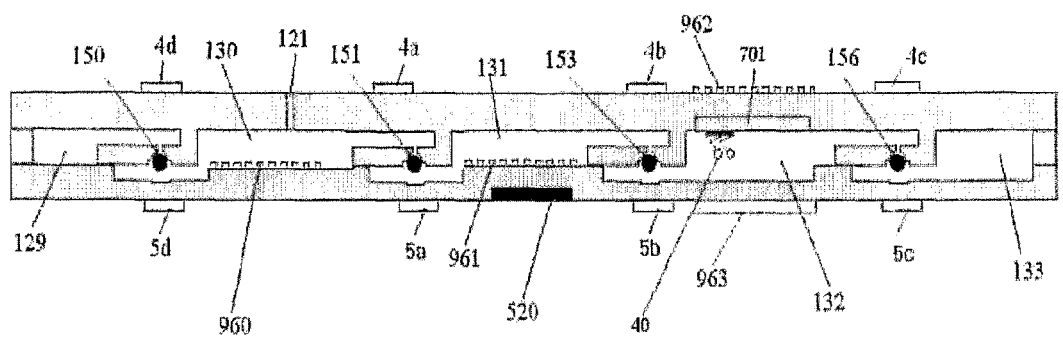

FIG. 19 is a sectional view of the bio-discs of FIGS. 15 and 16, illustrating the main assay processes conducted therein.

Permanent magnetic microbeads 150, 151, 153, and 156 are individually moved up and down to close and open channels by the magnetic force generated by respective permanent magnet and electromagnet pairs 4d and 5d, 4a and 5a, 4b and 5b, and 4c and 5c. Reference numeral 121 denotes a sample inlet.

In the preparation chamber 130, a DNA is prepared from blood, cells, or RNA. For this purpose, the preparation chamber 130 reserves a lysis buffer solution for DNA extraction through lysis and particles or ferroelectric beads having affinity to extracted DNA.

The PCR chamber 131 contains various enzymes, including a polymerase, dNTPs and a primer, which are required for PCR, in a buffer. In the assay site 132 where hybridization or antigen-antibody reaction takes place, capture probes for analyzing and diagnosing amplified DNA products from the PCR or immuno arrays are immobilized. Wastes from washing are collected in the trash chamber 133.

An embodiment of how to conduct main assay processes in the labs-on-a-chip of FIGS. 15, 16 and 19 will be described.

<Sample Preparation Process>

DNA is extracted from a sample in the preparation chamber 130 in the following way.

1) 10 µL (EDTA, ACD Tube) or 5 µL (heparin tube) of blood is injected via the sample inlet 121 into the preparation chamber 130 containing a lysis buffer solution and particles or ferroelectric beads having affinity to extracted DNA.

2) Five-min incubation is performed to extract DNA from the blood and allow the particles or ferroelectric beads to attract the extracted DNA.

3) Power is applied to the electromagnet 177 of FIG. 15 or a movable permanent magnet is moved close to the preparation chamber 130 to fix the particles or ferroelectric beads, followed by 1-3 min suspension.

4) The bio-disc is slowly rotated, the valve 161 is opened to allow the cell debris to flow into the trash chamber 153, followed by closing the valve 161 and stopping rotation of the bio-disc.

5) The power applied to the electromagnet 177 is cut off or the movable permanent magnet is moved away from the preparation chamber 130.

6) The valve 150 is opened and the bio-disc is slowly rotated to allow a washing buffer in the washing buffer reservoir 129 to flow into the preparation chamber 130.

7) Processes 2) through 6) are repeated twice, the bio-disc is slowly rotated, and the valve 161 is opened to fully wash the cell debris out and collect it in the trash chamber 135, followed by closing the valve 161 and stopping rotation of the bio-disc.

8) The power applied to the electromagnet 177 is cut off or the movable permanent magnet is moved away from the preparation chamber 130, the bio-disc is slowly rotated, and the valve 151 is opened to allow the distilled water in the reservoir 129a to flow into the preparation chamber 130.

9) A heater 960 installed in the preparation chamber 130 is turned on to separate DNA from the particles or electromagnetic beads or resuspend it in a resuspension buffer.

Alternatively, DNA can be extracted and separated from the blood by lysis buffer and contrifugal force without the particles or ferroelectric beads.

<PCR Process>

DNA amplification is conducted in the PCR chamber 131 or 131a in the following way.

1) The bio-disc is slowly rotated, the valve 152 is opened to allow the DNA separated from the electromagnetic beads in the preparation chamber 130 to flow into the PCR chamber 131.

2) Once the DNA reaches the PCR chamber 131, the valve 152 is closed, followed by stopping rotation of the bio-disc.

3) Thirty cycles of PCR are conducted using a heater 961 and a thermosensor 520 installed in the PCR chamber 131 to amplify DNA.

4) The PCR products were cooled for 1-2 minutes.

For a bio-disc with the structure of FIG. 16, the bio-disc is slowly rotated, the vale 152a is opened to migrate the PCR products from each of the PCR chambers 131 a into the chamber 131 b.

<Fragmentation Process>

Fragmentation, which is optional, is conducted to cut the amplified DNA products from the PCR to proper size for hybridization. The amplified DNA products may be fragmented as follows.

1) The bio-disc is slowly rotated, and the valve 158 is opened to allow a DNAse in the reservoir 136 to flow into the PCR chamber 131 (131a) for fragmentation.

2) The valve 158 is closed, followed by stopping rotation of the bio-disc.

3) After 1-2 min incubation, the heater 961 is turned on to deactivate the DNAse and stop the fragmentation. As a result, the DNA is denaturated into single strands.

The length of DNA fragments may be varied depending on the duration of incubation process 3). For the bio-disc of FIG. 16, which includes a plurality of PCR chambers with a separate heater in each PCR chamber 131a, the heaters are individually controlled during fragmentation to obtain DNA fragments which vary in length. It will be appreciated that the duration of the incubation can be varied in each PCR chamber <Hybridization Process>

Single-stranded DNA from the PCR, which has undergone high-temperature denaturation, optionally, has further undergone fragmentation into a proper size, is hybridized to biotin-labeled capture probes previously immobilized on the assay site 132 in the following way.

1) The bio-disc is slowly rotated, the valve 153 is opened to allow the single-stranded DNA to enter the assay site 132.

2) After the single-stranded DNA is allowed to spread over the assay site, the valve 153 is closed, rotating the bio-disc is stropped, and the bio-disc is incubated in a stationary state at room temperature for 3-5 minutes. Hybridization reaction is controlled by varying the electric field strength of an external electrode pattern 962 and an electrode plate 963 and the amount of heat generated by a heater 962. For reference, the electrode pattern 962 acts as a heater when operated alone but can also serve as an electrode plate generating a perpendicular electric field when operated in combination with the electrode plate 963.

3) The bio-disc is rotated, the valve 157 is opened to allow a hybridization buffer to flow into the assay site 132 for washing, with or without the application of an external electric field vertically through the bio-disc (first wash process). The valve 157 is closed. The valve 156 is opened during washing and closed after washing.

4) The bio-disc is slowly rotated, and the valve 154 is opened to allow a solution to enter and spread over the assay site 132.

The valve 154 is closed, and the bio-disc is incubated in a stationary state for 1-2 minutes to cleave single-stranded DNA (cleavage process).

5) The bio-disc is slowly rotated, and the valve 160 is opened to allow a PBS solution to enter the assay site 132 to wash out cleaved DNA fragments at 80° C., with or without the application of an external electric field to the bio-disc. After washing, the valve 160 is closed.

6) The bio-disc is slowly rotated, and the valve 155 is opened to allow a streptavidin-labeled metal microsphere suspension to enter and spread over the assay site 132 ("uncleaved probe-label complex" formation). In particular, the biotin-labeled capture probes are bound with the streptavidin-labeled metal microspheres 40, forming a biotin-streptavidin binding structure. Next, the valve 155 is closed.

During this process, the reaction temperature and the electric field strength may be controlled using the external electrode pattern 962 and the electrode plate 963. As described above, the electrode pattern 962 acts as a heater when operated alone but can also serve as an electrode plate generating a perpendicular electric field when operated in combination with the electrode plate 963.

7) The bio-disc is rotated at a higher speed, and the valve 162 is opened to allow distilled water in the reservoir 128 to enter the assay site for washing, with or without the application of an electric field to the bio-disc (second wash process). During this wash process, the valve 156 is opened.

<Detection Process>

Uncleaved signal elements remaining in the assay site 132 are detected using a detector including an optical device, an electrochemical device, a capacitance and impedance measurement device, or an image sensor, which have the above-described structure, the detector being programmed to be able to selectively detect assay sites with cleavable signal elements.

The diagnostic data and a questionnaire sheet based on the result of the detection are displayed on a computer monitor, and optionally automatically or manually transmitted through the Internet to a specialist at a remote location. The patient waits for a prescription from the specialist.

For the detailed descriptions on the cleavage, first wash, second wash, and remote diagnosis processes, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides," can be referred to.

FIG. 19 illustrates an embodiment of a bio-disc in which an electrochemical detector or a capacitance and impedance measurement device using the interdigitated array electrodes on the substrate 701 is installed as a detector in the assay site 132. Alternatively, a pair of optical assay detectors 99a and 99b of FIGS. 6 through 8 can be integrated into the bio-disc with various modification.

An embodiment of how to conduct main assay processes in the lab-on-a-chip of FIG. 17 will be described.

<Sample Preparation Process>

Serum is extracted from blood in the preparation chamber 130 in the following way.

1) 10 μL (EDTA, ACD Tube) of blood is injected via the sample inlet 121 into the preparation chamber 130. The bio disc is slowly rotated to separate a serum from a blood clot.

2) The valve 152 is opened, and the bio-disc is slowly rotated to allow the serum in the upper layer of the preparation chamber 130 to flow into the labeled antibody reservoir 142a.

3) Rotation of the bio-disc is stopped, and the valve 152 is closed.

<Antigen-Antibody Reaction>

The labeled antibody reservoir 142a of FIG. 17 reserves labeled antibodies labeled with coloring moiety, such as gold, latex, a fluorescent material, an enzyme, and a radioactive isotope and the assay site 132 contains capture antibodies immobilized on a substrate such as porous membrane.

Antigen-antibody reactions in a bio-disc according to the present invention involve binding an antigen in the serum extracted via the sample preparation to the labeled antibodies in the labeled antibody reservoir 142a to form a label-antigen complex and binding the label-antigen complex to the capture antibodies in the assay site 132. These antigen-antibody reactions are induced in the following way.

1) After the serum enters the labeled antibody reservoir chamber 142, the labeled antibody reservoir chamber 142 is incubated for 1-2 minutes to induce a reaction between an antigen and labeled antibodies to form a label-antigen complex.

2) The valve 153 is opened, the bio-disc is slowly rotated to allow the label-antigen complex in the labeled antibody reservoir 142a to flow into the assay site 132.

3) Rotation of the bio-disc is stopped, and the valve 153 is closed.

4) The bio-disc is incubated in a stationary state at room temperature for 3-5 minutes and left for a reaction between the label-antigen antibody and the capture antibodies in the assay site 132.

5) The bio-disc is rotated, and the valve 150 is opened to allow the washing buffer in the washing buffer reservoir 129 to enter and wash the assay site 132.

<Detection Process>

Uncleaved signal elements remaining in the assay site 132 are detected using a detector including an optical device, an electrochemical device, a capacitance and impedance measurement device, or an image sensor, which have the above-described structure, the detector being programmed to be able to selectively detect assay sites with cleavable signal elements.

The diagnostic data and a questionnaire sheet based on the result of the detection are displayed on a computer monitor, and optionally automatically or manually transmitted through the Internet to a specialist at a remote location. The patient waits for a prescription from the specialist.

Figure 20:
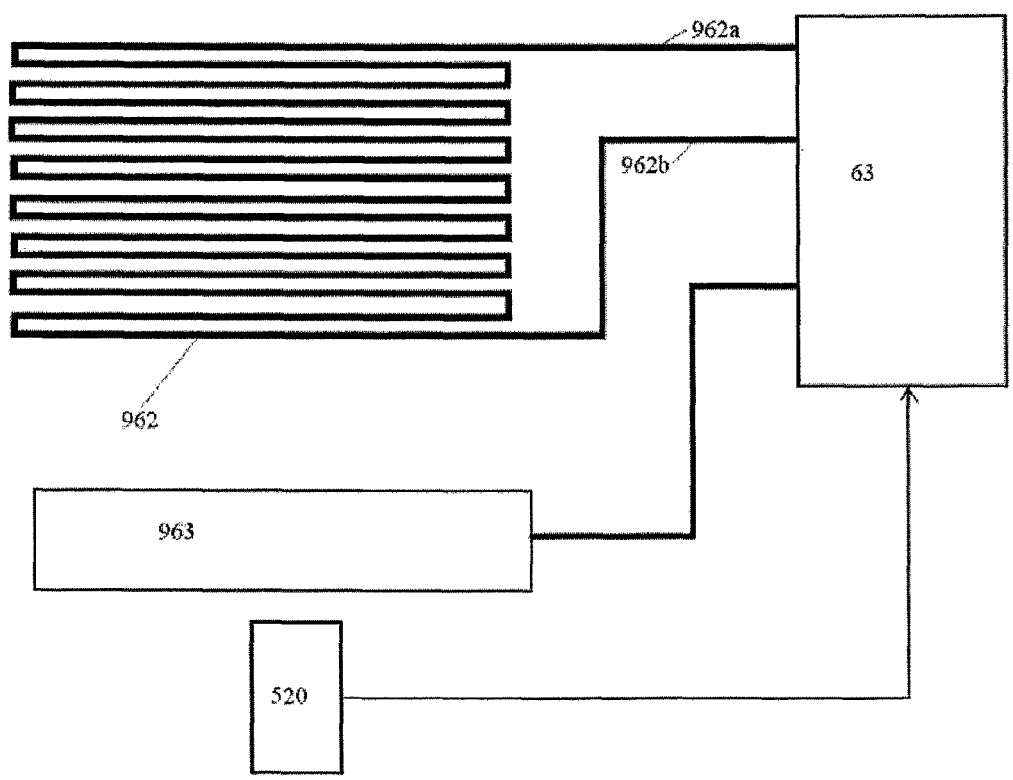

FIG. 20 illustrates an embodiment of a heater and an electric field generation used in sample preparation, PCR, and hybridization. The heaters 960, 961, and 962 in FIG. 19 are formed as an electrode pattern. As described above, the electrode pattern 962 acts as a heater when operated alone but can also serve as an electrode plate generating a perpendicular electric field when operated in combination with the electrode plate 963.

The reaction temperature and the electric field strength are controlled by the controller 63. As shown in FIG. 20, the electrode pattern 962 as a heater have two input ports 962a and 962b. A voltage is applied across the input ports 962a and 962b to induce current flow in the electrode pattern 961 and enable the electrode pattern 961 to act as a resistive or thermal coil.

The controller 63 supplies a current to the electrode pattern 962 via its input ports 962a and 962b and controls the amount of current supplied to the electrode pattern 962 and its temperature using the temperatures of the electrode pattern 962 periodically measured by the thermosensor 520. To operate the electrode pattern 962 as an electrical field generator in combination with the electrode pattern 963, an equal voltage is applied across the two input ports 962a and 962b of the electrode pattern 962 to handle them as one port, while a voltage is applied to the electrode plate 962 as the other port. In other words, the controller 63 applies an AC voltage across the electrode pattern 962 and the electrode plate 963 to generate an AC electric field. Since DNA has negative charges, the AC electric field strength between the electrode pattern 962 and the electrode plate 963 can be varied to control the stringency of DNA hybridization and for higher sensitivity in detecting single nucleotide polymorphism (SNP).

For the detailed description on SNP detection, International Patent Application No. PCT/KR02/00126 filed 27 Jan. 2002 and its priority Korean Patent Application No. 10-2001-0003956 filed 27 Jan. 2001, which are entitled "Nucleic acid hybridization assay method and device using cleavage technique responsive to complementary double strand or single strand of nucleic acids or oligonucleotides," can be referred to.

Although the thermosensor 520 of FIG. 19 is described as being used for precise temperature control during PCR, it can be used in any process which requires thermal detection.

An assay automatically starts as soon as a bio-disc is loaded into a bio-driver apparatus. When a bio-disc into which a sample has not been injected yet via the sample inlet is loaded, the bio-driver apparatus sends an "eject" message or a warning message to a user.

To determine whether a sample has been injected or not, an additional impedance measurement device may be installed in the preparation chamber 130. Whether a sample has been injected or not can be determined from different impedance characteristics between two states, one containing a sample and one without a sample.

Such an impedance measurement device for detecting the presence of a sample may be implemented with interdigitated array electrodes, like the capacitance and impedance measurement device installed in the assay site 132.

When an unloading or a stop command is input to the bio-driver apparatus during assay or diagnosis, the bio-driver apparatus sends a warning message or requests a user's password while continuing assay and diagnosis. If the user enters the correct password, the bio-driver apparatus stops the assay or diagnosis and ejects the bio-disc.

Once the assay or diagnosis is completed, the bio-driver apparatus ejects the bio-disc at the request of the user.

The bio-disc stores in its RFIC card 188 information on how many times it has been used, its validation period, and kinds of diseases which it can diagnose. For example, when an eject command is input to a disposable bio-disc during an assay or after the completion of an assay, the history of its use is written to its RFIC card 188 to later inform a user who loads the disposable bio-disc that it cannot be reused. When a bio-disc which has an expired validation term is loaded, the bio-driver apparatus informs the user that the bio-disc is no longer valid.

Figure 21:
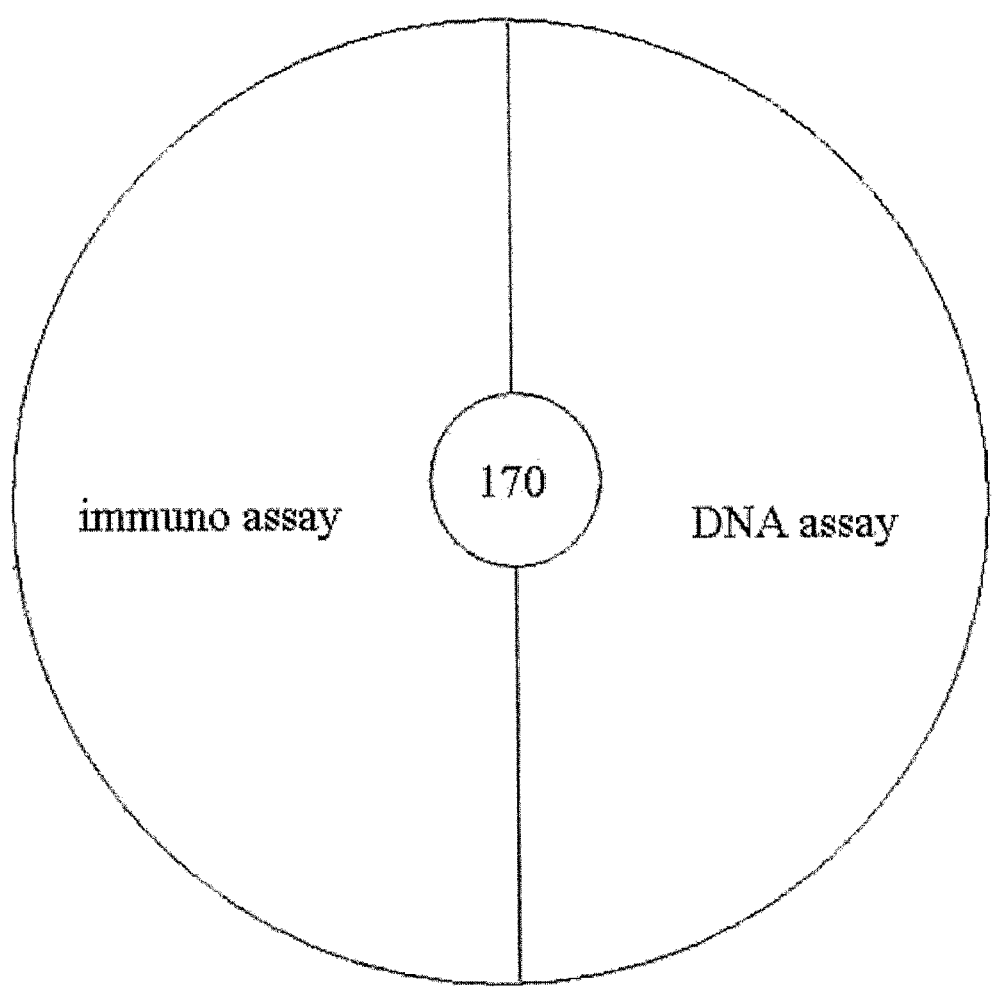
FIGS. 21 and 22 are views showing an arrangement of a bio-disc and an assay site used to simultaneously perform an immuno assay and a nucleic acid probe assay.
Figure 22:
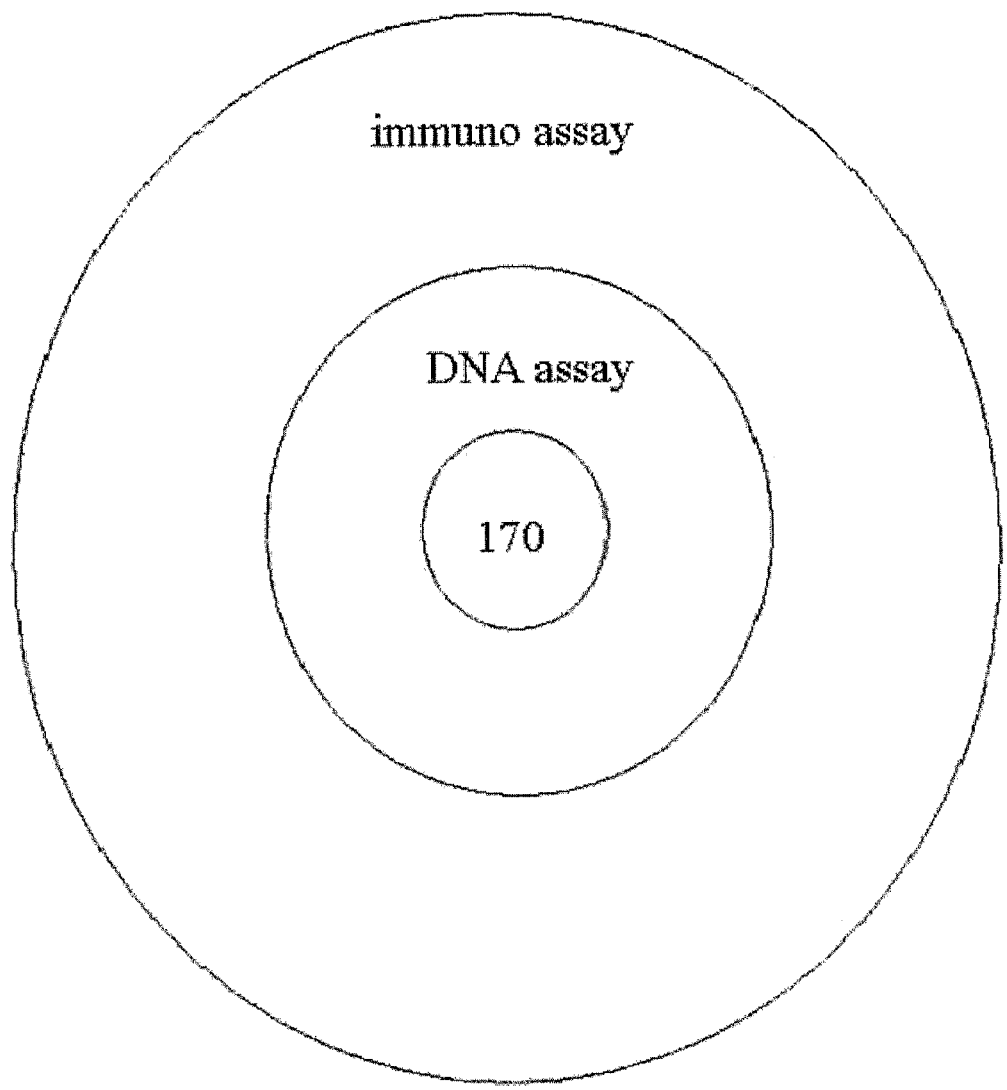

FIGS. 21 and 22 illustrate embodiments of assay devices according to the present invention, in which an immunoassay sector for antigen-antibody reaction and a nucleic acid probe hybridization sector are arranged in an angular or radial direction. An immunoassay and a DNA assay can be conducted simultaneously with the assay devices of FIGS. 21 and 22. In addition, the number of assay sites can be reduced through proper combination, and diagnostic reliability is doubled.

Figure 23:
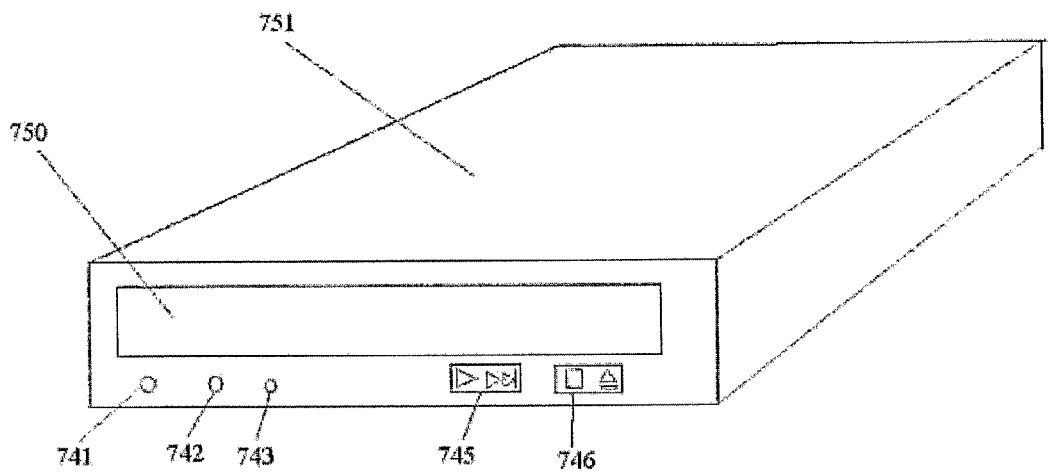
FIGS. 23 to 26 are views showing an outer appearance of a bio-disc driver apparatus according to the present invention.
Figure 24:
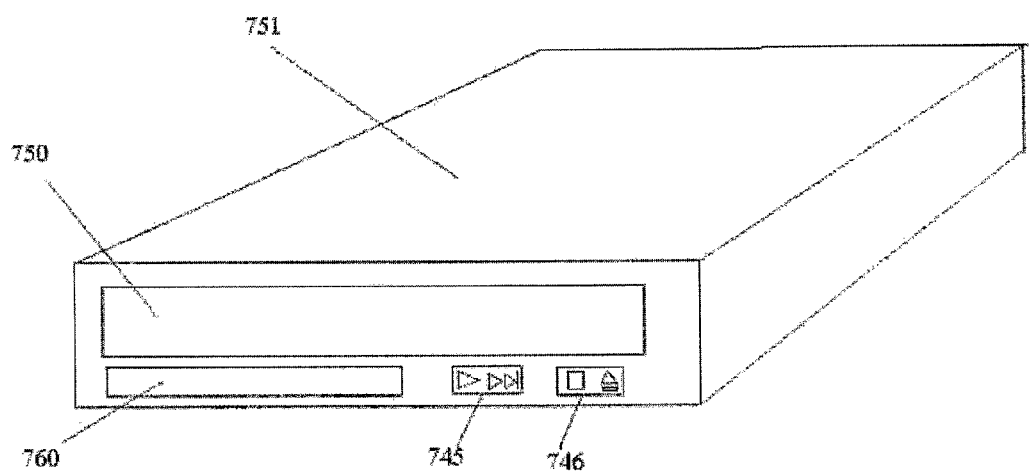

FIGS. 23 and 24 illustrate exemplary appearances of front loading-type bio-driver apparatuses according to the present invention. Reference numeral 751 denotes a case, reference numeral 750 denotes a bio-disc loading tray, and reference numerals 745 and 746 denote a button and a stop button, respectively, for general optical discs.

In particular, the bio-driver apparatus of FIG. 23 is an embodiment of indicating the status of proceeding with an assay using light emitting diodes (LEDs). A LED 741 indicates that a currently loaded disc is a bio-disc, a LED 742 indicates the current status of proceeding with an assay, and a LED 743 indicates that a general optical disc has been loaded. Alternative indicative means instead of LEDs can be used for the same purpose.

The bio-driver apparatus of FIG. 24 is an embodiment of indicating the status of proceeding with an assay through a liquid crystal display (LCD) 760. In this embodiment, the status of progress in each main process, such as sample preparation, PCR, hybridization, and antigen-antibody reaction, can be expressed in percentages or as a bar graph.

The status of proceeding with an assay in the bio drive apparatus according to the present invention can be displayed through a computer monitor or a graphic user interface. The status of progress in each main process, such as sample preparation, PCR, hybridization, and antigen-antibody reaction, can be expressed in percentages or as a bar or pie graph.

Figure 25:
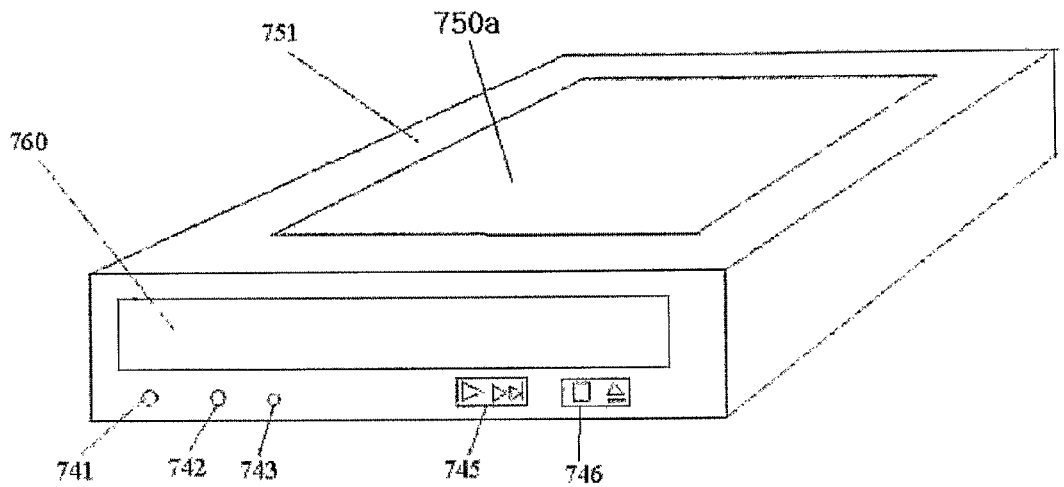

FIG. 25 illustrates an exemplary appearance of top loading-type bio-driver apparatuses according to the present invention. Reference numeral 751 denotes a case, reference numeral 750a denotes a bio-disc loading cover, and reference numerals 745 and 760 denote a liquid crystal display.

Figure 26:
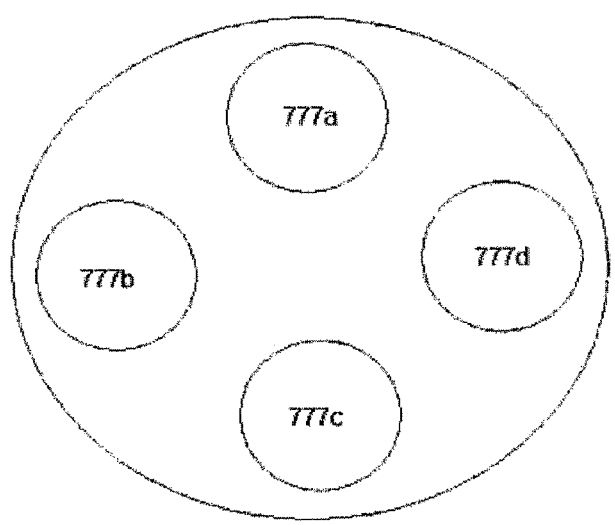

FIG. 26 illustrates an exemplary appearance of bio-driver apparatuses having a plurality of turn tables (777a, 777b, 777c, 777d) so as to load a plurality of the bio-discs in one time. In this case, 4 bio discs can be assayed in order or in one time.

In this embodiment, the status of progress in each main process, such as sample preparation, PCR, hybridization, and antigen-antibody reaction, can be expressed in percentages or as a bar graph.

The status of proceeding with an assay in the bio drive apparatus according to the present invention can be displayed through a computer monitor or a graphic user interface. The status of progress in each main process, such as sample preparation, PCR, hybridization, and antigen-antibody reaction, can be expressed in percentages or as a bar or pie graph.

Figure 27:
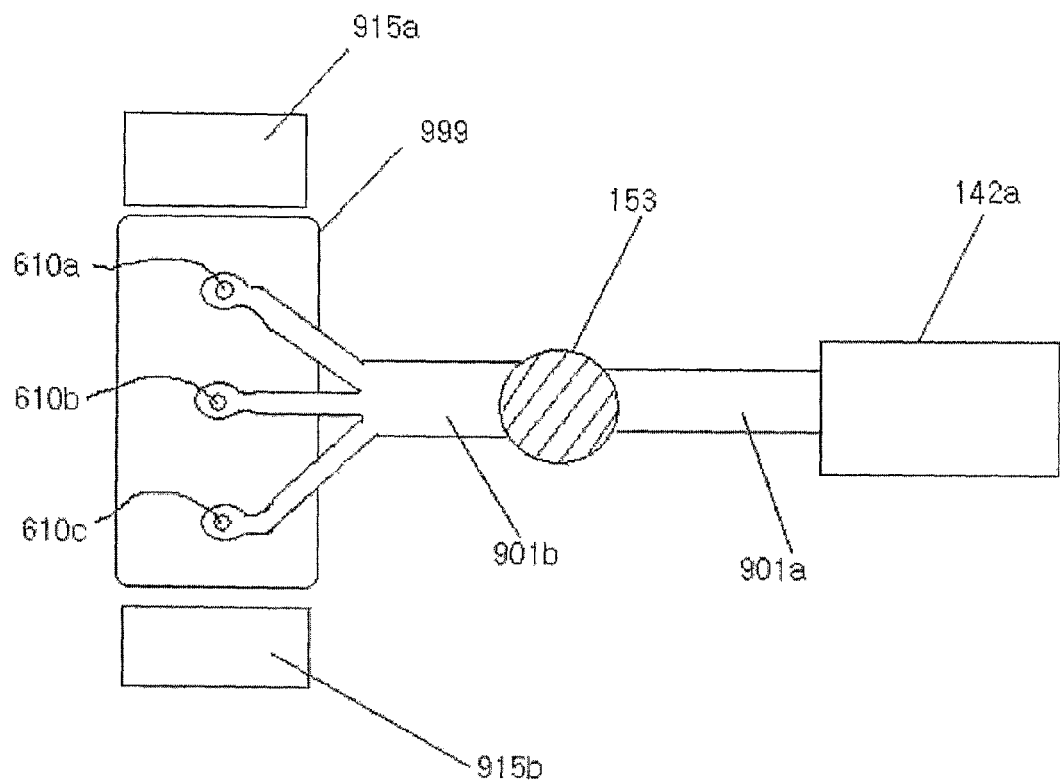
FIG. 27 is a view showing an arrangement of a assay site which is connected with a hydrophilic channel and a just-before valve according to an embodiment of the present invention.

FIG. 27 illustrates an embodiment of a assay site which is connected with a hydrophilic channel and a just-before valve according to the present invention. In FIG. 27, reference numeral 901a denotes a hydrophobic channel, reference numeral 901b denotes a hydrophilic channel and reference numeral 153 denotes a just-before valve of the assay site. Reference numeral 999 denotes a porous membrane fixed with capture antibodies in the assay site. In this embodiment, the hydrophilic channel 901b is divided into 3 branch channels, and the hydrophilic channel 901b is connected to the porous membrane 999 through holes 610a, 610b, 610c provided to a distal end of each branch channel. The assay site have air holes 915a and 915b disposed at the both sides of the assay site to dry the porous membrane 999 when the disc is rotated.

After antigens in the serum are bound with the labeled antibody in the label chamber 142a, label-antigen complexs are formed and flow into the hydrophic channel 901b and fill the branched channels when the valve 153 is opened. Next, the valve 153 is closed and the bio disc is slowly rotated to move the label-antigen complex into the porous membrane 999 through holes 610a, 610b, 610c provided to a distal end of each branch channel. And then, an antigen-antibody reaction between the label-antigen complex and the capture antibodies fixed in the porous membrane 999 is performed.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

As described above, a bio-disc device including a new valve control means and fluid movement system, a bio-driver apparatus, and an assay method using the same according to the present invention are suitable for labs-on-a-chip for various diagnostic assay devices, nucleic acid hybridization assay devices, and immunoassays. A particularly important feature of the present invention is that the bio-driver apparatus is compatible with general optical discs, including audio CDs, game CDs, including CD-ROMs, DVD players, etc. Thus, the present invention offers an economical and convenient alternative to conventional products. In addition, the bio-driver apparatus can be readily and easily applied in connection with a computer for remote diagnosis via the Internet.

Although a few embodiments have been shown and described, it would be appreciated by those skilled in the art that changes may be made in these embodiments without departing from the principles and spirit of the invention, the scope of which is defined in the claims and their equivalents.

The invention claimed is:

1. A bio-disc system comprising:
   a bio-disc and an optical pick up apparatus separately disposed under the bio-disc, said bio-disc comprising:
   a body sample inlet;
   an assay site where bio materials are arrayed on a substrate;
   channels through which fluid flows;
   a plurality of chambers which reserve a buffer solution or a reaction solution wherein the chambers are radially disposed through a series of the channels;
   holes which connect the channels; and
   valves which are used to open and close the holes, each valve comprising a microbead, a single moveable permanent magnet disposed under the microbead, and a fixed position permanent magnet disposed above the microbead, wherein the single movable permanent magnet is mounted on the optical pick up apparatus.

2. The bio-disc system according to claim 1, wherein the microbead is a film-like cylindrical magnet or a film-like cylindrical magnet coated with a cushion material.

3. The bio-disc system according to claim 1, wherein the substrate in the assay site is a porous membrane, and wherein an after channel of the assay site is a hydrophilic channel.

4. The bio-disc system according to claim 3, wherein the porous membrane is one selected from the group consisting of a NC (nitrocellose) membrane, a nylon membrane, and aligned nanotubes.

5. The bio-disc system according to claim 3, wherein the hydrophilic channel is constructed by coating a surface of a hydrophobic channel with a hydrophilic acrylate, an ultra-hydrophilic poly (N-isopropylacrylamide) (PIPAAm) or an optical catalyst selected from the group consisting $ZrO_2$, $ZnO$, $Fe_2O_3$, and $TiO_2$ or by performing a surface modification on the hydrophobic channel with plasma.

6. The bio-disc system according to claim 3, wherein the hydrophilic channel is divided into at least one branch channel, and the hydrophilic channel is connected to the porous membrane through a hole provided to a distal end of the branch channel.

7. The bio-disc system according to claim 3, wherein the assay site has air holes to dry the porous membrane.

8. The bio-disc system according to claim 1, wherein the fluid movement is controlled by a centrifugal force due to rotation of the bio-disc and opening and closing of the valves.

9. The bio-disc system according to claim 1, the bio materials are at least one selected from DNA, oligo-nucleotide, RNA, PNA, ligand, receptor, antigen, antibody, and protein.

10. The bio-disc system according to claim 1, wherein the chambers comprise at least one selected from the group consisting of: a preparation chamber for preparing a DNA sample from blood, cells, or RNA; a PCR chamber for amplifying the DNA sample through a polymerase chain reaction (PCR); a label chamber for reserving a label indicator; a hybridization chamber in which assay and diagnostic probes are arrayed on the substrate for hybridization with the amplified DNA from the PCR; and a trash chamber for collecting wastes generated from washing.

11. The bio-disc system according to claim 10, wherein the preparation chamber reserves a lysis buffer solution used to destruct a cell and extract a DNA through lysis and particles or ferromagnetic beads having affinity to the extracted DNA.

12. The bio-disc system according to claim 10, wherein the bio-disc comprises a plurality of the PCR chambers and each PCR chamber reserves one type or several types of primer or all the PCR chambers reserves the same type of primer.

13. The bio-disc system according to claim 1, wherein the chambers comprise at least one chamber selected from the group consisting of: a preparation chamber for preparing a serum sample, an antigen, or an antibody from blood or cells; an antigen-antibody reaction chamber in which immuno probes are arrayed on the substrate for an antigen-antibody reaction with the prepared antigen or antibody; and a trash chamber for collecting waste generated from washing.

14. The bio-disc system according to claim 13, wherein the serum sample in the preparation chamber is prepared by using a centrifugal force generated by rotation of the disc.

15. The bio-disc system according to claim 14, wherein the preparation chamber has a shape of a conical beaker or a flask in order to facilitate separating serum in centrifugal separation and a channel at a neck portion in order to be connected to a next chamber.

16. The bio-disc system according to claim 13, wherein the chambers further comprise a label chamber for reserving a labeled antibody.

17. The bio-disc system according to claim 16, wherein the label of the labeled antibody has gold, latex, a fluorescent material, an enzyme, or a radioactive isotope as a coloring particle.

18. The bio-disc system according to claim 13, wherein the immuno probe array is constructed by arraying tumor markers on a substrate.

19. The bio-disc system according to claim 18, wherein the tumor marker is at least one selected from AFP, PSA, CEA, CA19-9, CA125, and CA15-3.

20. The bio-disc system according to claim 13, wherein the immuno probes are at least one selected from myoglobin, CK-MB, and Troponin I (TnI) as a cardiac infraction marker and Glutamine Synthetase (GS) as an Alzheimer's disease marker.

21. The bio-disc system according to claim 1, wherein the assay site is detected by a detection device coupled with a transforming device and the detection device includes a light transmission type measuring device, an electro-chemical detection device, a capacitance and impedance measuring device, or an image sensor.

22. The bio-disc system according to claim 21, wherein the light transmission type detection device comprises: a laser device which emits a laser beam onto a confined signal element and a released signal element; and an optical detector which detects a differential light transmission signal between the signal elements.

23. The bio-disc system according to claim 22, wherein the optical detector is arrayed and integrated along a circumference of the bio-disc to correspond to the assay site.

24. The bio-disc system according to claim 22, wherein the laser device and the optical detector are arrayed and integrated along a circumference of the bio-disc to correspond to the assay site.

25. The bio-disc system according to claim 21, wherein the electro-chemical detection device or the capacitance and impedance measuring device comprises: interdigitated array electrodes disposed on the substrate of the assay site; and an HRP (Horse Radish Peroxidase) and/or enzyme and/or a metal micro-sphere attached to the end of confined signal elements.

26. The bio-disc system according to claim 25, wherein the interdigitated array electrodes are constructed by coating a surface of a porous membrane with a conductive material.

27. The bio-disc system according to claim 21, wherein the image sensor is constructed with a CCD (charge coupled Device) sensor or a Complementary Metal-Oxide Semiconductor (CMOS) sensor with or without a fluorescent filter to pick up an image of a label linked with the probe in the assay site.

28. The bio-disc system according to claim 1, wherein the assay site comprises an immuno assay sector and a nucleic acid probe assay sector arranged in an angular or radial direction to enable an immuno assay and a nucleic acid probe assay to be performed concurrently.

29. The bio-disc system according to claim 10, which further comprises an impedance measuring device or an image sensor in the preparation chamber in order to detect a sample injection.

30. The bio-disc system according to claim 29, wherein the impedance measuring device is an interdigitated array.

31. The bio-disc system according to claim 1, wherein the bio-disc is constructed with an upper substrate, an intermediate substrate, and a lower substrate, and these substrates are adhered and assembled by using ultrasonic fusing, UV adhesive, or double-sided tape to form a single body.

32. The bio-disc system according to claim 1, which further comprises a memory or radio frequency integrated circuit (RF IC) storing a protocol of the bio-disc, assay interpretive algorithms, standard control values for analysis, positional information on analysis sites, bioinformatics information, self-diagnostics information, bio-disc driver software, educational information for patients on clinical assays, a variety of web sites and links enabling a patient to communicate with a doctor or hospital at a remote location based on his/her diagnosis result, or encrypted personal information.

33. The bio-disc system according to claim 1, which further comprises statistic software and storage managing a history of detection results of the assay site and provides periodical diagnosis information to a user.

34. The bio-disc system according to claim 1, which further comprises a controller disc including a controller which supplies power or a control signal to the bio-disc; and an interfacing zone for connecting the bio-disc and the controller disc.

35. The bio-disc system according to claim 34, wherein the interfacing zone comprises: a plurality of control signal nodes through which the control signal is supplied; and/or a power node through which power is supplied.

36. The bio-disc system according to claim 35, the interfacing zone comprises: grooves formed in the bio-disc and coated with a conductive material; and conductive arms protruding from the controller disc and engaging the grooves.

37. The bio-disc system according to claim 34, wherein the controller disc is fixed to a turntable on which the bio-disc is mounted and further include an electromagnetic magnet or a movable permanent magnet for controlling a valve embedded in the bio-disc.

38. The bio-disc system according to claim 34, wherein a gap between the bio-disc and the controller disc is in a range of from 0.1 mm to 2 mm.

39. The bio-disc system according to claim 34, wherein the power is supplied to the controller disc through a brush or an electrical contact connected to an external power supply.

40. The bio-disc system according to claim 34, wherein the controller disc comprises an integrated circuit in a printed circuit board (PCB) or in a silicon wafer.

41. The bio-disc system according to claim 34, wherein the controller disc further comprises a non-contact interface selected from among an infrared interface, an optical interface, and a wireless interface to transmit the result of a detection from the assay site by a detector to an external central control system, a storage unit, or an input output unit via the non-contact interface.

42. The bio-disc system according to claim 34, wherein the bio-disc and the controller disc are integrated as a single body to form a controller disc-combined bio-disc.

43. The bio-disc system according to claim 42, wherein the controller disc-combined bio-disc has a monolithic circuit structure integrated into a silicon wafer via photolithography and etching processes, the monolithic circuit structure including the controller, a radio frequency integrated circuit (RF IC), a non-contact interface, an electrode plate or electromagnet for valve control, various circuit patterns, chambers, and channels.

44. A nucleic acid assay method comprising:
introducing blood, cells, or RNA to the bio-disc system of claim 10, wherein the system performs the steps of:
preparing a DNA sample from the blood, cells, or RNA;
amplifying the prepared DNA through polymerase chain reaction (PCR);
hybridizing amplified DNA products from the PCR to the assay and diagnostic probe arrayed on the assay site; and
detecting a result of hybridization reaction in the assay site by using a detection device coupled with a transforming device, wherein the detection device includes a light transmission type measuring device, an electro-chemical detection device, a capacitance or impedance measuring device, or an image sensor.

45. An immuno assay method comprising:
introducing blood to the bio-disc system of claim 16, wherein the system performs the steps of:
rotating the bio-disc at high speed to extract serum or an antigen from the blood;
introducing the extracted antigen into a label chamber and performing incubation in the chamber for 1-2 minutes to bind the antigen to labeled antibodies and form a label-antigen complex;
moving the label-antigen complex into the assay site; and
performing cultivation in the bio-disc in a stationary state to induce an antigen-antibody reaction between the label-antigen complex and the capture antibodies; and
adding a washing buffer and washing the assay site.

46. The immuno assay method according to claim 45, which further comprises picking up an image with an image sensor in order to detect a result of an antigen-antibody reaction in the assay site.

47. The immuno assay method according to claim 45, which further comprises performing remote transmission of the result of the antigen-antibody together with a questionnaire sheet to a specialist at a remote location.

* * * * *

UNITED STATES PATENT AND TRADEMARK OFFICE
CERTIFICATE OF CORRECTION

PATENT NO.        : 8,993,487 B2
APPLICATION NO.   : 11/919567
DATED             : March 31, 2015
INVENTOR(S)       : Jae Chern Yoo It is certified that error appears in the above-identified patent and that said Letters Patent is hereby corrected as shown below:

Claims

Claim 32, Column 31, Line 39-40 (Approximately)
Delete "(RF IC)" and insert --(RFIC)--, therefor.

Claim 43, Column 32, Line 26-27 (Approximately)
Delete "(RF IC)" and insert --(RFIC)--, therefor.

Signed and Sealed this
Twentieth Day of October, 2015

Michelle K. Lee
*Director of the United States Patent and Trademark Office*